United States Patent
Kassis et al.

(10) Patent No.: US 10,626,464 B2
(45) Date of Patent: Apr. 21, 2020

(54) METHODS OF DETECTING PROSTATE CANCER

(71) Applicant: Cell MDX, LLC, Corvallis, OR (US)

(72) Inventors: Amin I. Kassis, Chesnut Hill, MA (US); Harry Stylli, La Jolla, CA (US); Colleen Kelly, Carlsbad, CA (US); Geoffrey Erickson, Corvallis, OR (US); Kirk J. Wojno, Royal Park, MI (US)

(73) Assignee: Cell MDX, LLC, Corvallis, OR (US)

( * ) Notice: Subject to any disclaimer, the term of this patent is extended or adjusted under 35 U.S.C. 154(b) by 0 days.

(21) Appl. No.: 15/510,948

(22) PCT Filed: Sep. 11, 2015

(86) PCT No.: PCT/US2015/049751
§ 371 (c)(1),
(2) Date: Mar. 13, 2017

(87) PCT Pub. No.: WO2016/040843
PCT Pub. Date: Mar. 17, 2016

(65) Prior Publication Data
US 2017/0275704 A1    Sep. 28, 2017

Related U.S. Application Data

(60) Provisional application No. 62/049,281, filed on Sep. 11, 2014.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57434* (2013.01); *C12Q 2600/118* (2013.01);
(Continued)

(58) Field of Classification Search
CPC .......... C12Q 1/6883; C12Q 1/6886; C12Q 2600/16; C12Q 2600/118;
(Continued)

(56) References Cited

U.S. PATENT DOCUMENTS

| | | |
|---|---|---|
| 4,683,195 A | 7/1987 | Mullis et al. |
| 4,683,202 A | 7/1987 | Mullis |

(Continued)

FOREIGN PATENT DOCUMENTS

| | | |
|---|---|---|
| WO | WO 1994/016101 | 7/1994 |
| WO | WO 2001/014881 | 3/2001 |

(Continued)

OTHER PUBLICATIONS

Jung, V. et al. Journal of Urology 189(4 Suppl 1):e545 (Abstract No. 1334). Apr. 2013.*
(Continued)

*Primary Examiner* — Diana B Johannsen
(74) *Attorney, Agent, or Firm* — Casimir Jones, S.C.; Tanya Arenson

(57) ABSTRACT

The invention described herein provides biological markers for the diagnosis, prognosis, and monitoring of prostate cancer.

9 Claims, 2 Drawing Sheets

(52) U.S. Cl.
CPC . *C12Q 2600/136* (2013.01); *C12Q 2600/158* (2013.01); *G01N 2500/04* (2013.01); *G01N 2500/10* (2013.01); *G01N 2800/50* (2013.01); *G01N 2800/52* (2013.01)

(58) Field of Classification Search
CPC ........ C12Q 2600/136; C12Q 2600/156; C12Q 2600/158; G01N 33/5023; G01N 33/6803; G01N 33/56966; G01N 33/57434; G01N 2500/04; G01N 2500/10; G01N 2570/00; G01N 2800/50; G01N 2800/52
See application file for complete search history.

(56) References Cited

U.S. PATENT DOCUMENTS

| | | |
|---|---|---|
| 4,843,155 A | 6/1989 | Chomczynski |
| 4,868,103 A | 9/1989 | Stavrianopoulos et al. |
| 5,459,039 A | 10/1995 | Modrich et al. |
| 5,498,531 A | 3/1996 | Jarrell |
| 5,514,598 A | 5/1996 | Doody |
| 5,594,637 A | 1/1997 | Eisenberg et al. |
| 5,631,169 A | 5/1997 | Lakowicz et al. |
| 5,854,033 A | 12/1998 | Lizardi |
| 6,172,198 B1 | 1/2001 | Sinosich |
| 6,258,540 B1 | 7/2001 | Lo et al. |
| 6,631,330 B1 | 10/2003 | Poynard |
| 6,660,477 B2 | 12/2003 | Kluwe |
| 6,664,056 B2 | 12/2003 | Lo et al. |
| 6,986,995 B2 | 1/2006 | Rose et al. |
| 7,009,038 B2 | 3/2006 | Depre et al. |
| 7,157,235 B2 | 1/2007 | Breit et al. |
| 7,235,359 B2 | 6/2007 | Lo et al. |
| 7,294,465 B2 | 11/2007 | Somlo et al. |
| 7,432,107 B2 | 10/2008 | Spanuth |
| 7,445,886 B2 | 11/2008 | Giroir et al. |
| 7,459,280 B2 | 12/2008 | Wang et al. |
| 7,488,584 B2 | 2/2009 | Wang et al. |
| 7,604,948 B2 | 10/2009 | Amaral et al. |
| 7,645,576 B2 | 1/2010 | Lo et al. |
| 7,651,838 B2 | 1/2010 | Paterlini-Brechot |
| 7,655,399 B2 | 2/2010 | Cantor et al. |
| 7,662,578 B2 | 2/2010 | Devarajan |
| 7,670,764 B2 | 3/2010 | Oh et al. |
| 2001/0051341 A1 | 12/2001 | Lo et al. |
| 2002/0045176 A1 | 4/2002 | Lo et al. |
| 2002/0119118 A1 | 8/2002 | Fong et al. |
| 2002/0192642 A1 | 12/2002 | Lo et al. |
| 2004/0009518 A1 | 1/2004 | Lo et al. |
| 2004/0086864 A1 | 5/2004 | Lo et al. |
| 2004/0110221 A1 | 6/2004 | Twine et al. |
| 2004/0137452 A1 | 7/2004 | Levett et al. |
| 2004/0203037 A1 | 10/2004 | Lo et al. |
| 2005/0130245 A1 | 6/2005 | Houle et al. |
| 2005/0164233 A1 | 7/2005 | Byrne et al. |
| 2005/0164241 A1 | 7/2005 | Hahn et al. |
| 2005/0266432 A1 | 12/2005 | Oliphant et al. |
| 2005/0282185 A1 | 12/2005 | Lo Yuk-Ming et al. |
| 2006/0019278 A1 | 1/2006 | Lo et al. |
| 2006/0115854 A1 | 6/2006 | Goldknopf et al. |
| 2006/0115855 A1 | 6/2006 | Goldknopf et al. |
| 2006/0166283 A1 | 7/2006 | Delacourte et al. |
| 2006/0210562 A1 | 9/2006 | Zaghouani et al. |
| 2006/0234301 A1 | 10/2006 | Dotan et al. |
| 2006/0252068 A1 | 11/2006 | Lo et al. |
| 2006/0252071 A1 | 11/2006 | Lo et al. |
| 2006/0257901 A1 | 11/2006 | Karumanchi |
| 2006/0259990 A1 | 11/2006 | Von Der Kammer et al. |
| 2006/0259991 A1 | 11/2006 | Von Der Kammer et al. |
| 2007/0141625 A1 | 6/2007 | Santos et al. |
| 2007/0148661 A1 | 6/2007 | Vance et al. |
| 2007/0162983 A1 | 7/2007 | Hesterkamp et al. |
| 2007/0207466 A1 | 9/2007 | Cantor et al. |
| 2007/0218469 A1 | 9/2007 | Navon |
| 2007/0218519 A1 | 9/2007 | Urdea et al. |
| 2007/0224638 A1 | 9/2007 | Melanitou-McClymont |
| 2007/0264197 A1 | 11/2007 | Lamping et al. |
| 2007/0275402 A1 | 11/2007 | Lo et al. |
| 2008/0026378 A1 | 1/2008 | Bottazzo et al. |
| 2008/0026405 A1 | 1/2008 | Lovell et al. |
| 2008/0038730 A1 | 2/2008 | Von Der Kammer et al. |
| 2008/0039402 A1 | 2/2008 | Mossalayi et al. |
| 2008/0051334 A1 | 2/2008 | Pohlner et al. |
| 2008/0152589 A1 | 6/2008 | Schofield et al. |
| 2008/0153090 A1 | 6/2008 | Lo et al. |
| 2008/0220013 A1 | 9/2008 | Hochstrasser et al. |
| 2008/0227709 A1 | 9/2008 | Pascual et al. |
| 2008/0261217 A1 | 10/2008 | Melnikov et al. |
| 2008/0261226 A1 | 10/2008 | Wang et al. |
| 2008/0261258 A1 | 10/2008 | Smith et al. |
| 2008/0269103 A1 | 10/2008 | Von Der Kammer et al. |
| 2008/0286263 A1 | 11/2008 | Leeds et al. |
| 2009/0023166 A1 | 1/2009 | Jeannin et al. |
| 2009/0041862 A1 | 2/2009 | Schofield et al. |
| 2009/0054321 A1 | 2/2009 | O'Neill et al. |
| 2009/0061425 A1 | 3/2009 | Lo et al. |
| 2009/0110667 A1 | 4/2009 | Mozaffarian et al. |
| 2009/0130683 A1 | 5/2009 | Gaffney et al. |
| 2009/0155230 A1 | 6/2009 | Salonen et al. |
| 2009/0155776 A1 | 6/2009 | Lo et al. |
| 2009/0162842 A1 | 6/2009 | Lo et al. |
| 2009/0170102 A1 | 7/2009 | Lo et al. |
| 2009/0176217 A1 | 7/2009 | Sella-Tavor et al. |
| 2009/0196927 A1 | 8/2009 | Panitch et al. |
| 2009/0202469 A1 | 8/2009 | Maruyama et al. |
| 2009/0239241 A1 | 9/2009 | Ray et al. |
| 2009/0239242 A1 | 9/2009 | Kilty et al. |
| 2009/0258025 A1 | 10/2009 | Godowski et al. |
| 2009/0263474 A1 | 10/2009 | Banchereau et al. |
| 2009/0274709 A1 | 11/2009 | Xu et al. |
| 2009/0275046 A1 | 11/2009 | Goldknopf et al. |
| 2009/0305265 A1 | 12/2009 | Snider et al. |
| 2009/0317797 A1 | 12/2009 | Paterlini et al. |
| 2009/0318354 A1 | 12/2009 | Cahill et al. |
| 2009/0318392 A1 | 12/2009 | Oresic et al. |
| 2009/0324611 A1 | 12/2009 | Eriksson |
| 2010/0009352 A1 | 1/2010 | Gough et al. |
| 2010/0009356 A1 | 1/2010 | Snider et al. |
| 2010/0021929 A1 | 1/2010 | Pow |
| 2010/0028356 A1 | 2/2010 | Schofield et al. |
| 2010/0055722 A1 | 3/2010 | Nayak et al. |
| 2010/0062463 A1 | 3/2010 | Bergmann et al. |
| 2010/0068705 A1 | 3/2010 | Helgadottir et al. |
| 2010/0068711 A1 | 3/2010 | Umansky et al. |
| 2010/0075891 A1 | 3/2010 | Ayalon-Soffer et al. |
| 2010/0081142 A1 | 4/2010 | Chen et al. |
| 2010/0092983 A1 | 4/2010 | Liew |
| 2010/0098705 A1 | 4/2010 | Eugen-Olsen et al. |
| 2010/0104579 A1 | 4/2010 | Hubner et al. |
| 2010/0105086 A1 | 4/2010 | Landolfo et al. |
| 2010/0105623 A1 | 4/2010 | Weinberger et al. |
| 2010/0112587 A1 | 5/2010 | Hare et al. |
| 2010/0120041 A1 | 5/2010 | Quaggin |
| 2010/0120050 A1 | 5/2010 | Gadkar et al. |
| 2010/0120056 A1 | 5/2010 | Bar-Or et al. |
| 2010/0120076 A1 | 5/2010 | Braun et al. |
| 2010/0120629 A1 | 5/2010 | Ellis et al. |
| 2010/0124746 A1 | 5/2010 | Liew |
| 2010/0124756 A1 | 5/2010 | Ray et al. |
| 2010/0131286 A1 | 5/2010 | Houlgatte et al. |
| 2010/0137164 A1 | 6/2010 | Rubin et al. |
| 2010/0137263 A1 | 6/2010 | Smith |
| 2010/0137393 A1 | 6/2010 | Bottazzo et al. |
| 2010/0143951 A1 | 6/2010 | Kronenberg et al. |
| 2010/0159486 A1 | 6/2010 | Liotta et al. |
| 2010/0167320 A1 | 7/2010 | Beernink et al. |
| 2010/0167937 A1 | 7/2010 | Goldknopf et al. |
| 2010/0169988 A1 | 7/2010 | Kohli et al. |
| 2012/0021404 A1 | 1/2012 | Melkonyan et al. |
| 2012/0230953 A1 | 9/2012 | Goldenberg et al. |
| 2013/0023426 A1 | 1/2013 | Kassis |
| 2014/0179805 A1 | 6/2014 | Stylli |
| 2016/0025733 A1 | 1/2016 | Stylli |

(56) References Cited

U.S. PATENT DOCUMENTS

| | | |
|---|---|---|
| 2016/0119226 A1 | 4/2016 | Guichard et al. |
| 2016/0281168 A1 | 9/2016 | Stylli |
| 2016/0036935 A1 | 12/2016 | Kassis |
| 2017/0044626 A1 | 2/2017 | Kassis |

FOREIGN PATENT DOCUMENTS

| | | |
|---|---|---|
| WO | WO 2002/068685 | 9/2002 |
| WO | WO 2003/019193 | 3/2003 |
| WO | WO 2004/024098 | 3/2004 |
| WO | WO 2004/040016 | 5/2004 |
| WO | WO 2004/047758 | 6/2004 |
| WO | WO 2004/050704 | 6/2004 |
| WO | WO 2004/071269 | 8/2004 |
| WO | WO 2004/076639 | 9/2004 |
| WO | WO 2004/079012 | 9/2004 |
| WO | WO 2005/007836 | 1/2005 |
| WO | WO 2005/012907 | 2/2005 |
| WO | WO 2005/033341 | 4/2005 |
| WO | WO 2005/052592 | 6/2005 |
| WO | WO 2005/103712 | 11/2005 |
| WO | WO 2005/111626 | 11/2005 |
| WO | WO 2005/114222 | 12/2005 |
| WO | WO 2006/020269 | 2/2006 |
| WO | WO 2006/020899 | 2/2006 |
| WO | WO 2006/026020 | 3/2006 |
| WO | WO 2006/048778 | 5/2006 |
| WO | WO 2006/050475 | 5/2006 |
| WO | WO 2006/061609 | 6/2006 |
| WO | WO 2006/073941 | 7/2006 |
| WO | WO 2006/105907 | 10/2006 |
| WO | WO 2006/114661 | 11/2006 |
| WO | WO 2006/125117 | 11/2006 |
| WO | WO 2006/133423 | 12/2006 |
| WO | WO 2006/134390 | 12/2006 |
| WO | WO 2007/047907 | 4/2007 |
| WO | WO 2007/082733 | 7/2007 |
| WO | WO 2007/098585 | 9/2007 |
| WO | WO 2007/112999 | 10/2007 |
| WO | WO 2007/119179 | 10/2007 |
| WO | WO 2007/131345 | 11/2007 |
| WO | WO 2008/003826 | 1/2008 |
| WO | WO 2008/010660 | 1/2008 |
| WO | WO 2008/014314 | 1/2008 |
| WO | WO 2008/014516 | 1/2008 |
| WO | WO 2008/028257 | 3/2008 |
| WO | WO 2008/042012 | 4/2008 |
| WO | WO 2008/043725 | 4/2008 |
| WO | WO 2008/043782 | 4/2008 |
| WO | WO 2008/046509 | 4/2008 |
| WO | WO 2008/046510 | 4/2008 |
| WO | WO 2008/046511 | 4/2008 |
| WO | WO 2008/046512 | 4/2008 |
| WO | WO 2008/063369 | 5/2008 |
| WO | WO 2008/064336 | 5/2008 |
| WO | WO 2008/082519 | 7/2008 |
| WO | WO 2008/084331 | 7/2008 |
| WO | WO 2008/085035 | 7/2008 |
| WO | WO 2008/089936 | 7/2008 |
| WO | WO 2008/095261 | 8/2008 |
| WO | WO 2008/100596 | 8/2008 |
| WO | WO 2008/120684 | 10/2008 |
| WO | WO 2008/125651 | 10/2008 |
| WO | WO 2008/127317 | 10/2008 |
| WO | WO 2008/129296 | 10/2008 |
| WO | WO 2008/132464 | 11/2008 |
| WO | WO 2008/137835 | 11/2008 |
| WO | WO 2008/147938 | 12/2008 |
| WO | WO 2008/154238 | 12/2008 |
| WO | WO 2008/156867 | 12/2008 |
| WO | WO 2009/000520 | 12/2008 |
| WO | WO 2009/001392 | 12/2008 |
| WO | WO 2009/003142 | 12/2008 |
| WO | WO 2009/014639 | 1/2009 |
| WO | WO 2009/017444 | 2/2009 |
| WO | WO 2009/032722 | 3/2009 |
| WO | WO 2009/034470 | 3/2009 |
| WO | WO 2009/043848 | 4/2009 |
| WO | WO 2009/050444 | 4/2009 |
| WO | WO 2009/053523 | 4/2009 |
| WO | WO 2009/053537 | 4/2009 |
| WO | WO 2009/055487 | 4/2009 |
| WO | WO 2009/058168 | 5/2009 |
| WO | WO 2009/059259 | 5/2009 |
| WO | WO 2009/060035 | 5/2009 |
| WO | WO 2009/068591 | 6/2009 |
| WO | WO 2009/074331 | 6/2009 |
| WO | WO 2009/075566 | 6/2009 |
| WO | WO 2009/075579 | 6/2009 |
| WO | WO 2009/080780 | 7/2009 |
| WO | WO 2009/083950 | 7/2009 |
| WO | WO 2009/092068 | 7/2009 |
| WO | WO 2009/092382 | 7/2009 |
| WO | WO 2009/097450 | 8/2009 |
| WO | WO 2009/100131 | 8/2009 |
| WO | WO 2009/100342 | 8/2009 |
| WO | WO 2009/121152 | 10/2009 |
| WO | WO 2009/121951 | 10/2009 |
| WO | WO 2009/122387 | 10/2009 |
| WO | WO 2009/127644 | 10/2009 |
| WO | WO 2010/005750 | 1/2010 |
| WO | WO 2010/011506 | 1/2010 |
| WO | WO 2010/012306 | 2/2010 |
| WO | WO 2010/018185 | 2/2010 |
| WO | WO 2010/019553 | 2/2010 |
| WO | WO 2010/022210 | 2/2010 |
| WO | WO 2010/025434 | 3/2010 |
| WO | WO 2010/039714 | 4/2010 |
| WO | WO 2010/041046 | 4/2010 |
| WO | WO 2010/046137 | 4/2010 |
| WO | WO 2010/046503 | 4/2010 |
| WO | WO 2010/048346 | 4/2010 |
| WO | WO 2010/048347 | 4/2010 |
| WO | WO 2010/048497 | 4/2010 |
| WO | WO 2010/053587 | 5/2010 |
| WO | WO 2010/054167 | 5/2010 |
| WO | WO 2010/054389 | 5/2010 |
| WO | WO 2010/059242 | 5/2010 |
| WO | WO 2010/059996 | 5/2010 |
| WO | WO 2010/061283 | 6/2010 |
| WO | WO 2010/063009 | 6/2010 |
| WO | WO 2010/065940 | 6/2010 |
| WO | WO 2010/066000 | 6/2010 |
| WO | WO 2010/068686 | 6/2010 |
| WO | WO 2012/012693 | 1/2012 |
| WO | WO 2012/012694 | 1/2012 |
| WO | WO 2012/012704 | 1/2012 |
| WO | WO 2012/012709 | 1/2012 |
| WO | WO 2012/012714 | 1/2012 |
| WO | WO 2012/012717 | 1/2012 |
| WO | WO 2012/012725 | 1/2012 |
| WO | WO 2012/016332 | 2/2012 |
| WO | WO 2012/115885 | 8/2012 |
| WO | WO 2013/003384 | 1/2013 |
| WO | WO 2013/188846 | 12/2013 |
| WO | WO 2014/164362 | 10/2014 |
| WO | WO 2014/164366 | 10/2014 |
| WO | WO 2016/040843 | 3/2016 |

OTHER PUBLICATIONS

Abravaya et al., Detection of point mutations with a modified ligase chain reaction (Gap-LCR), Nucleic Acids Res. 23:675-682 (1995).
Allen, Modulating phagocyte activation: the pros and cons of Helicobacter pylori virulence factors. J Exp Med. 191(9):1451-4 (2000).
Archacki et al., Expression profiling of cardiovascular disease., Human Genomics, 1(5):355-370 (2004).
Avagyan, et al., Immune Blood Biomarkers of Alzheimer Disease Patients, Journal of Neuroimmunology, 210:67-72 (2009).
Baker, The central role of receiver operating characteristic (ROC) curves in evaluating tests for the early detection of cancer, Journal of the National Cancer Institute, 95(7):511-515 (2003).

(56) References Cited

OTHER PUBLICATIONS

Balagurumoorthy et al., Genome-subtractive cancer-specific blood assay, Cancer Research, AACR Annual Meeting, Apr. 18-22, 2009. Abstract #2562.
Barany, Genetic disease detection and DNA amplification using cloned thermostable ligase, Proc. Natl. Acad. Sci. USA 88:189-193 (1991).
Bergsmedh et al., DNase II and the Chk2 DNA damage pathway form a genetic barrier blocking replication of horizontally transferred DNA. Mol Cancer Res. 4(3):187-95 (2006).
Bidwell et al., Silencing of Irf7 pathways in breast cancer cells promotes bone metastasis through immune escape, Nature Medicine, 18:1224-1231 (2012).
Biswas et al., A distinct and unique transcriptional program expressed by tumor-associated macrophages (defective NF-kappaB and enhanced IRF-3/STAT1 activation). Blood. Mar. 1, 2006;107(5):2112-22.
Bitterman et al., Alveolar Macrophage Replication: One Mechanism for the Expansion of the Mononuclear Phagocyte Population in the Chronically Inflamed Lung. J Clin Invest., 74:460-469 (1984.
Caruso et al., Neutrophil-tumor cell phagocytosis (cannibalism) in human tumors: an update and literature review, Exp. Oncol., 34(3):306-311 (2012).
Chakraborty et al., A spontaneous murine melanoma lung metastasis comprised of host x tumor hybrids. Cancer Res. May 1, 2000;60(9):2512-9.
Cheung, M., et al., Prenatal Diagnosis of Sickle Cell Anemia and Thalassaemia by Analysis of Fetal Cells in Maternal Blood, Nature Genetics, 14:264-268 (1996).
Chiu et al., Noninvasive prenatal diagnosis of fetal chromosomal aneuploidy by massively parallel genomic sequencing of DNA in maternal plasma, Proc Natl Acad Sci USA, 105:20458-20463 (2008).
Choudhury et al., The role of genetic markers in the management of prostate cancer. Eur Urol. Oct. 2012;62(4):577-87.
Cohen et al., Emerging technologies for sequencing antisense oligonucleotides: capillary electrophoresis and mass spectrometry, Adv. Chromatogr., 36:127-162 (1996).
Colcher et al., A spectrum of monoclonal antibodies reactive with human mammary tumor cells. Proc Natl Acad Sci U S A. May 1981;78(5):3199-203.
Colcher et al., Prolonged binding of a radiolabeled monoclonal antibody (B72.3) used for the in situ radioimmunodetection of human colon carcinoma xenografts. Cancer Res. Dec. 1984;44(12 Pt 1):5744-51.
Coleman, Of mouse and man—what is the value of the mouse in predicting gene expression in humans, Drug D Discovery Today, 8:233-235 (2003).
Cotton et al., Reactivity of cytosine and thymine in single-base-pair mismatches with hydroxylamine and osmium tetroxide and its application to the study of mutations, Proc. Natl. Acad. Sci., 85:4397-4401 (1988).
Cotton, Current methods of mutation detection, Mutat. Res., 285:125-144 (1993).
Cronin et al., Cystic fibrosis mutation detection by hybridization to light-generated DNA probe arrays, Human Mutation, 7:244-255 (1996).
Denmeade et al., Concentration of Enzymatically Active Prostate-Specific Antigen (PSA) in the Extracellular Fluid of Primary Human Prostate Cancers and Human Prostate Cancer Xenograft Models, The Prostate. 48:1-6 (2001).
Du et al., Genomic profiles for human peripheral blood T cells, B cells, natural killer cells, monocytes, and polymorphonuclear cells: comparisons to ischemic stroke, migraine, and Tourette syndrome. Genomics. Jun. 2006;87(6):693-703.
Efron, Empirical Bayes Estimates for Large-Scale Prediction Problems, J Am Stat Assoc, 104:1015-1028 (2009).
Engels, Infectious Agents as Causes of Non-Hodgkin Lymphoma, Cancer Epidemiol Biomarkets Prev, 16:401-404 (2007).
Enhfors et al., Horizontal transfer of tumor DNA to endothelial cells in vivo, Cell Death Differ., 16:749-757 (2009).

Gasparini et al., Restriction site generating-polymerase chain reaction (RG-PCR) for the probeless detection of hidden genetic variation: application to the study of some common cystic fibrosis mutations, Mol. Cell Probes, 6:1-7 (1992).
Gautier et al, Affy—analysis of Affymetrix GeneChip data at the probe level, Bioinformatics, 20:307-315 (2004).
Gibbs et al., Detection of single DNA base differences by competitive oligonucleotide priming, Nucl. Acids Res., 17:2437-2438 (1989).
Ginos et al., Identification of a gene expression signature associated with recurrent disease in squamous cell carcinoma of the head and neck. Cancer Res. Jan. 1, 2004;64(1):55-63.
Glinsky et al., Gene expression profiling predicts clinical outcome of prostate cancer. J Clin Invest. Mar. 2004;113(6):913-23.
Griffin et al., DNA sequencing. Recent innovations and future trends, Appl. Biochem. Biotechnol., 38:147-159 (1993).
Grigoriadis et al., Establishment of the epithelial-specific transcriptome of normal and malignant human breast cells based on MPSS and array expression data. Breast Cancer Res. 2006;8(5):R56.
Guatelli et al., Isothermal, in vitro amplification of nucleic acids by a multienzyme reaction modeled after retroviral replication, Proc. Natl. Acad. Sci. USA 87:1874-1878 (1990).
Guha, Keshava D., Sciences develop novel cancer blood test, Apr. 28, 2009, The Harvard Crimson [online], retrieved on Jun. 18, 2014], Retrieved from the internet: http://www.thecrimson.com/article/2009/4/28/scientists-develop-novel-cancer-blood-test/, 2 pages.
Haakenson et al., HDAC6 and ovarian cancer.Int J Mol Sci. May 2, 2013;14(5):9514-35.
Hage et al., Recent advances in chromatographic and electrophoretic methods for the study of drug-protein interactions, J. Chromatogr. B. Biomed. Sci. Appl., 12:499-525 (1997).
Haupl et al., Reactivation of Rheumatoid Arthritis After Pregnancy; Arthritis and Rheumatism, 58:2981-2992 (2008).
Hayashi, PCR-SSCP: a method for detection of mutations, Genet. Anal. Tech. Appl., 9:73-79 (1992).
Heegaard, Capillary electrophoresis for the study of affinity interactions, J. Mol. Recognit., 11 :141-148 (1998).
Herwig et al., Ability of PSA-positive circulating macrophages to detect prostate cancer, The Prostate, 62:290-298 (2005).
Herwig et al., Measurement of intracellular versus extracellular prostate-specific antigen levels in peripheral macrophages: a new approach to noninvasive diagnosis of prostate cancer, Clinical Prostate Cancer, 3:184-188 (2004).
Holmgren et al., Horizontal transfer of DNA by the uptake of apoptotic bodies. Blood. Jun. 1, 1999;93(11):3956-63.
Hoshikawa et al., Hypoxia induces different genes in the lungs of rats compared with mice. Physiol Genomics. Feb. 6, 2003;12(3):209-19.
Hsu et al., Detection of DNA point mutations with DNA mismatch repair enzymes, Carcinogenesis, 15:1657-1662 (1994).
Huber et al., Variance Stabilization Applied to Microarray Data Calibration and to the Quantification of Differential Expression, Bioinformatics, vol. 1 B, Suppl. 1, S96-S104 (2002).
Kang et al., Adenoviral gene transfer of Caenorhabditis elegans n-3 fatty acid desaturase optimizes fatty acid composition in mammalian cells, Proc. Natl. Acad. Sci., 98:4050-4054 (2001).
Kang et al., Essential fatty acid metabolism in cultured human airway epithelial cells, Biochim. Biophys. Acta., 1128:267-274 (1992).
Kassis et al., Antibody-dependent signal amplification in tumor xenografts after pretreatment with biotinylated monoclonal antibody and avidin or streptavidin. J Nucl Med. Feb. 1996;37(2):343-52.
Keen et al., Rapid detection of single base mismatches as heteroduplexes on Hydrolink gels, Trends Genet., 7:5 (1991).
Kozal et al., Extensive polymorphisms observed in HIV-1 clade B protease gene using high-density oligonucleotide arrays, Nature Medicine, 2:753-759 (1996).
Kravtsov et al., Flow cytofluorometric assay of human whole blood leukocyte DNA degradation in response to Yersinia pestis and *Staphylococcus aureus*. Proceedings of SPIE, 4241:260-267 (2001).
Kravtsov, A., et al., Flow cytofluorometric assay of human whole blood leukocyte DNA degradation in response to Yersinia Pestis and *Staphylococcus Aureus*, Abstract.

(56) References Cited

OTHER PUBLICATIONS

Kwoh et al., Transcription-based amplification system and detection of amplified human immunodeficiency virus type 1 with a bead-based sandwich hybridization format, Proc. Natl. Acad. Sci.,86:1173-1177 (1989).
Landegran et al., A ligase-mediated gene detection technique, Science 241:1077-1080 (1988).
Lau et al., CD163: a specific marker of macrophages in paraffin-embedded tissue samples. Am J Clin Pathol. Nov. 2004;122(5):794-801.
Lee, Analysis issues for gene expression array data. Clin Chem. Aug. 2001;47(8):1350-2.
Li et al., Replacing PCR with COLD-PCR enriches variant DNA sequences and redefines the sensitivity of genetic testing, Nat. Med. 14:579-584 (2008).
Lin et al., Decreased Expression of Cellular Prostatic Acid Phosphatase Increases Tumorigenicity of Human Prostate Cancer Cells, The Journal of Urology, 166:1943-1950 (2001).
Linehan et al., The Genetics Basis of Cancer of the Kidney, The Journal of Urology, 170:2163-2172 (2003).
Liotta et al., Cancer's Deadly Signature, Nature Genetics, 33:1-10 (2003).
Liu et al., Comparison of differentially expressed genes in T lymphocytes between human autoimmune disease and murine models of autoimmune disease, Clinical Immunology, 112:225-230 (2004).
Liu, Mechanism-derived gene expression signatures and predictive biomarkers in clinical oncology. Proc Natl Acad Sci U S A. Mar. 8, 2005;102(10):3531-2.
Lizardi et al. Exponential amplification of recombinant—RNA hybridization probes, Bio/Technology 6:1197-1202 (1988).
Lobenhofer et al., Progress in the application of DNA microarrays, Environmental Health Perspectives, 109:881-891 (2001).
Locke et al., Androgen levels increase by intratumoral de novo steroidogenesis during progression of castration-resistant prostate cancer. Cancer Res. Aug. 1, 2008;68(15):6407-15.
Loring et al., A Gene Expression Profile of Alzheimer's Disease, DNA and Cell Biology, 20:683-695 (2001).
Martin et al., Expression of the transcription factors snail, slug, and twist and their clinical significance in human breast cancer, Ann Surg Oncol., 12(6):488-96 (2005).
Maxam et al., A new method for sequencing DNA, Proc. Natl. Acad. Sci., 74:560-564 (1977).
McLaren et al., Antigen-specific gene expression profiles of peripheral blood mononuclear cells do not reflect those of T-lymphocyte subsets. Clin Diagn Lab Immunol. Sep. 2004;11(5):977-82.
McLerran, D., et al., Analytical Validation of Serum Proteomic Profiling for Diagnosis of Prostate Cancer: Sources of Sample Bias, Clinical Chemistry, 54:1, 44-52, 2008.
Michiels et al., Prediction of cancer outcome with microarrays: a multiple random validation strategy, Lancet, 365:488-492 (2005).
Myers et al., Detection of single base substitutions by ribonuclease cleavage at mismatches in RNA:DNA duplexes, Science, 230:1242-1246 (1985).
Myers et al., Detection of single base substitutions in total genomic DNA, Nature, 313:495-498 (1985).
Naeve et al., Accuracy of automated DNA sequencing: a multi-laboratory comparison of sequencing results, Biotechniques 19:448-453 (1995).
Nakagawa et al., A tissue biomarker panel predicting systemic progression after PSA recurrence post-definitive prostate cancer therapy. PLoS One. 2008;3(5):e2318.
Nakazawa et al., UV and skin cancer: specific p53 gene mutation in normal skin as a biologically relevant exposure measurement, Proc. Natl. Acad. Sci., 91:360-364 (1994).
Nanni et al., Differential gene expression profiling in genetic and multifactorial cardiovascular diseases. J Mol Cell Cardiol. Dec. 2006;41(6):934-48.

Orita et al., Detection of polymorphisms of human DNA by gel electrophoresis as single-strand conformation polymorphisms, Proc. Natl. Acad. Sci., 86:2766-2770 (1989).
Palmer et al., Cell-type specific gene expression profiles of leukocytes in human peripheral blood. BMC Genomics. May 16, 2006;7:115.
Perou et al., Molecular portraits of human breast tumors, Nature, 406:747-752 (2000).
Powell, Harvard gazette. Apr. 20, 2009, available via url: news.harvard.edu/gazette/story/2009/04/hms-professor-devises-single-test-for-cancers/>.
Prodromou et al., Recursive PCR: a novel technique for total gene synthesis, Protein Eng. 5:827-829(1992).
Prossner, Detecting single-base mutations, Tibtech, 11:238-246 (1993).
Ransohoff, Bias as a threat to the validity of cancer molecular-marker research, Nature, 5:142-149 (2005).
Rivas et al., New developments in the study of biomolecular associations via sedimentation equilibrium, Trends Biochem. Sci., 18:284-287 (1993).
Rogler et al., Isolation and phenotypic characterization of colonic macrophages. Clin Exp Immunol. May 1998;112(2):205-15.
Rosenbaum et al., Temperature-gradient gel electrophoresis. Thermodynamic analysis of nucleic acids and proteins in purified form and in cellular extracts. Biophys Chem. May 9, 1987;26(2-3):235-46.
Saiki et al., Analysis of enzymatically amplified beta-globin and HLA-DQ alpha DNA with allele-specific oligonucleotide probes, Nature, 324:163-166 (1986).
Saiki et al., Genetic analysis of amplified DNA with immobilized sequence-specific oligonucleotide probes, Proc. Natl. Acad. Sci. ,86:6230-6234 (1989).
Saleeba et al., Chemical cleavage of mismatch to detect mutations, Methods Enzymol., 217:286-295 (1992).
Sanger et al., DNA sequencing with chain-terminating inhibitors, Proc. Natl. Acad. Sci., 74:5463-5467 (1977).
Schiller et al., Lipid analysis by matrix-assisted laser desorption and ionization mass spectrometry: A methodological approach, Anal. Biochem., 267:46-56 (1999).
Schiller et al., Matrix-assisted laser desorption and ionization time-of-flight (MALDI-TOF) mass spectrometry in lipid and phospholipid research, Progress in Lipid Research, 43:449-488.
Segelmark et al., Autoimmune kidney diseases, Autoimmunity Reviews, 9:A366-A371 (2010).
Sehnert et al., Optimal detection of fetal chromosomal abnormalities by massively parallel DNA sequencing of cell-free fetal DNA from maternal blood, Clin Chem., 57:1042-1049 (2011).
Seo et al., Probe set algorithms: is there a rational best bet? BMC Bioinformatics. Aug. 30, 2006;7:395.
Sjolander et al., Integrated fluid handling system for biomolecular interaction analysis, Anal. Chem. 63:2338-2345 (1991).
Slonim, From patterns to pathways: gene expression data analysis comes of age, Nature Genetics Supplement, 32:502-508 (2002).
Srivastava et al., The Inflammatory versus Constitutive Trafficking of Mononuclear Phagocytes into the Alveolar Space of Mice is Associated with Drastic Changes in Their Gene Expression Profiles, J Immunology, 175:1884-1893 (2005).
Strachan et la., Chromosomes in Cells, Ch. 2 in NCBI Bookshelf, 1999, 16 pages.
Szabo et al., Surface plasmon resonance and its use in biomolecular interaction analysis (BIA), Curr. Opin. Struct. Biol., 5:699-705 (1995).
Takahashi et al., Gene expression profiling of clear cell renal cell carcinoma: gene identification and prognostic classification. Proc Natl Acad Sci U S A. Aug. 14, 2001;98(17):9754-9.
Taylor et al., Flow cytometric analysis of blood monocytes and alveolar macrophages. Methods Mol. Med., 44:67-80(2000).
Thisted (1998) What Is a P-Value. University of Chicago. May 25, 1998. Accessed from http://www.stat.uchIcago.eduHhisted, 6 pages.
Tsuang et al., Assessing the Validity of Blood-Based Gene Expression Profiles for the Classification of Schizophrenia and Bipolar Disorder: A Preliminary Report; American Journal of Medical Genetics Part B Neuropsychiatric Genetics) 1338:1 (2005).

(56) References Cited

OTHER PUBLICATIONS

Van 'T Veer et al., Expression profiling predicts outcome in breast cancer. Breast Cancer Res. 2003;5(1):57-8.
Vendrell et al., A20/TNFAIP3, a new estrogen-regulated gene that confers tamoxifen resistance in breast cancer cells, Oncogene, 26(32):4656-67 (2007).
Wachsman et al., Noninvasive genomic detection of melanoma, Br J Dermatol., 164:797-806 (2011).
Webb, Researchers explore role of gene transfer in tumor growth, J. Natl., Cancer Inst., 94(6):413-414 (2002).
West et al., Embracing the complexity of genomic data for personalized medicine, Genome Research, 16:559-566 (2006).
Weylandt et al., Polyunsaturated fatty acids exert antiarrhythmic actions as free acids rather than in phospholipids, Lipids, 31:977-982 (1996).
White, Identification and Mechanistic Investigation of Recurrent Function Genomic and Transcriptional Alterations in Advanced Prostate Cancer. Doctoral Dissertation, University of Washington, 2013, 152 pages.
Whitney et al., Individuality and variation in gene expression patterns in human blood. Proc Natl Acad Sci U S A. Feb. 18, 2003;100(4):1896-901.
Wu et al., A Model Based Background Adjustment for Oligonucleotide Expression Arrays, Journal of the American Statistical Assoc., 99:909-917.
Yang et al., Circumvention of normal constraints on granule protein gene expression in peripheral blood neutrophils and monocytes of patients with antineutrophil cytoplasmic autoantibody-associated glomerulonephritis. J Am Soc Nephrol. Aug. 2004;15(8):2103-14.
Zakynthinos et al., Inflammatory biomarkers in coronary artery disease, Journal of Cardiology, 53:317-333 (2009).
Zamora, et al., The Hematologist, Scientific Psychic Poster, 2007.
Zimmet et al., Polyploidy: occurrence in nature, mechanisms, and significance for the megakaryocyte-platelet system, Experimental hematology, 28: 3-16 (2000).
Extended European Search Report for EP 14779587.6, dated Nov. 28, 2016, 16 pages.
Extended European Search Report for EP 18153917.2, dated Sep. 21, 2018, 15 pages.
Extended European Search Report for EP 15840505.0, dated May 14, 2018, 12 pages.
International Search Report and Written Opinion for PCT/US2014/022149, dated Jul. 9, 2014, 30 pages.
International Search Report and Written Opinion for PCT/US2014/022139, dated Jul. 18, 2014, 36 pages.
International Search Report and Written Opinion for PCT/US2014/049751, dated Feb. 4, 2016, 16 pages.

* cited by examiner

METHODS OF DETECTING PROSTATE CANCER

RELATED APPLICATION

This application is the national stage filing under 35 U.S.C. § 371 of International Application No. PCT/US2015/049751 (now pending), filed Sep. 11, 2015, which claims priority and benefit from U.S. Provisional Patent Application 62/049,281, filed Sep. 11, 2014. The contents and disclosures of each of the foregoing patent applications are incorporated herein by reference in their entirety.

FIELD OF THE INVENTION

This invention relates generally to using biological markers for the diagnosis, prognosis, and monitoring of prostate cancer.

BACKGROUND OF THE INVENTION

Early diagnosis of prostate cancer often increases the likelihood of successful treatment or cure of such disease. Current diagnostic methods, however, depend largely on population-derived average values obtained from healthy individuals. Personalized diagnostic methods are needed that enable the diagnosis, especially the early diagnosis, of the presence of prostate cancer in individuals who are not known to have the cancer or who have recurrent prostate cancer.

Leukocytes begin as pluripotent hematopoietic stem cells in the bone marrow and develop along either the myeloid lineage (monocytes, macrophages, neutrophils, eosinophils, and basophils) or the lymphoid lineage (T and B lymphocytes and natural killer cells). The major function of the myeloid lineage cells (e.g., neutrophils and macrophages) is the phagocytosis of infectious organisms, live unwanted damaged cells, senescent and dead cells (apoptotic and necrotic), as well as the clearing of cellular debris. Phagocytes from healthy animals do not replicate and are diploid, i.e., have a DNA content of 2n. On average, each cell contains <10 ng DNA, <20 ng RNA, and <300 ng of protein. Non-phagocytic cells are also diploid and are not involved in the internalization of dead cells or infectious organisms and have a DNA index of one.

The lifetime of various white blood cell subpopulations varies from a few days (e.g., neutrophils) to several months (e.g., macrophages). Like other cell types, leukocytes age and eventually die. During their aging process, human blood- and tissue-derived phagocytes (e.g., neutrophils) exhibit all the classic markers of programmed cell death (i.e., apoptosis), including caspase activation, pyknotic nuclei, and chromatin fragmentation. These cells also display a number of "eat-me" flags (e.g., phosphatidylserine, sugars) on the extracellular surfaces of their plasma membranes. Consequently, dying and dead cells and subcellular fragments thereof are cleared from tissues and blood by other phagocytic cells.

The prostate specific antigen is currently one of the most widely used diagnostic measures used to detect prostate cancer. However, false negatives and false negatives are common, resulting in mistreatment of patients with no prostate cancer or overtreatment of patients with non-lethal prostate cancer. Thus, improved methods for detecting prostate cancer are needed.

SUMMARY OF THE INVENTION

In one aspect, the present invention provides methods for detecting or diagnosing prostate cancer by using at least one or more markers selected from Signature 1 (Table 1) and/or Signature 2 (Table 2) and/or Signature 3 (Table 3) and/or Signature 4 (Table 4). Levels (e.g., gene expression levels, protein expression levels, or activity levels) of the selected markers may be measured from a blood sample, or a portion of a blood sample (e.g., macrophages and non-phagocytes), from a subject. Such levels then can be compared, e.g., the levels of the selected markers in the phagocytic cells and in the non-phagocytic cells to identify one or more differences between the measured levels, indicating whether the subject has prostate cancer. The identified difference(s) can also be used for assessing the risk of developing prostate cancer, prognosing prostate cancer, monitoring prostate cancer progression or regression, assessing the efficacy of a treatment for prostate cancer, or identifying a compound capable of ameliorating or treating prostate cancer.

In yet another aspect, the levels of the selected markers in the phagocytic cells may be compared to the levels of the selected markers in a control (e.g., a normal or healthy control subject, or a normal or healthy cell from the subject) to identify one or more differences between the measured levels, indicating whether the subject has prostate cancer, the prognosis of the cancer and the monitoring of the cancer. The identified difference(s) can also be used for assessing the risk of developing prostate cancer, prognosing prostate cancer, monitoring prostate cancer progression or regression, assessing the efficacy of a treatment for prostate cancer, or identifying a compound capable of ameliorating or treating prostate cancer. Some embodiments of the invention are:

1. A method for diagnosing or aiding in the diagnosis of prostate cancer in a subject, the method comprising the steps of:

a) measuring the levels of one or more markers selected from the group consisting of Signature 1 markers in a population of the subject's macrophage cells;

b) measuring the levels of the one or more selected Signature 1 markers in a population of the subject's non-phagocytic cells; and c) identifying a difference between the measured levels of the one or more selected Signature 1 markers in steps a) and b), wherein the identified difference indicates that the subject has said prostate cancer.

2. A method for assessing the risk of developing prostate cancer in a subject, the method comprising the steps of:

a) measuring the levels of one or more markers selected from the group consisting of Signature 1 markers in a population of the subject's macrophage cells;

b) measuring the levels of the one or more selected Signature 1 markers in a population of the subject's non-phagocytic cells; and c) identifying a difference between the measured levels of the one or more selected Signature 1 markers in steps a) and b), wherein the identified difference indicates that the subject has a risk of developing said prostate cancer.

3. A method for prognosing or aiding in the prognosis of prostate cancer in a subject, the method comprising the steps of:

a) measuring the levels of one or more markers selected from the group consisting of Signature 1 markers in a population of the subject's macrophage cells;

b) measuring the levels of the one or more selected Signature 1 markers in a population of the subject's non-phagocytic cells; and c) identifying a difference between the measured levels of the one or more selected Signature 1 markers in steps a) and b), wherein the identified difference is indicative of the prognosis of said prostate cancer in the subject.

4. A method for assessing the efficacy of a treatment for prostate cancer in a subject comprising:

a) measuring the levels of one or more markers selected from the group consisting of Signature 1 markers in a population of the subject's macrophage cells before the treatment;

b) measuring the levels of the one or more selected Signature 1 markers in a population of the subject's non-phagocytic cells before the treatment;

c) identifying a first difference between the measured levels of the one or more selected Signature 1 markers in steps a) and b);

d) measuring the levels of the one or more selected Signature 1 markers in a population of the subject's macrophage cells after the treatment;

e) measuring the levels of the one or more selected Signature 1 markers in a population of the subject's non-phagocytic cells after the treatment;

f) identifying a second difference between the measured levels of the one or more selected Signature 1 markers in steps d) and e); and g) identifying a difference between the first difference and the second difference, wherein the difference identified in g) is indicative of the efficacy of the treatment for said prostate cancer in the subject.

5. A method for monitoring the progression or regression of prostate cancer in a subject comprising:

a) measuring the levels of one or more markers selected from the group consisting of Signature 1 markers in a population of the subject's macrophage cells at a first time point;

b) measuring the levels of the one or more selected Signature 1 markers in a population of the subject's non-phagocytic cells at the first time point;

c) identifying a first difference between the measured levels of the one or more selected Signature 1 markers in steps a) and b);

d) measuring the levels of the one or more selected Signature 1 markers in a population of the subject's macrophage cells at a second time point;

e) measuring the levels of the one or more selected Signature 1 markers in a population of the subject's non-phagocytic cells at the second time point;

f) identifying a second difference between the measured levels of the one or more selected Signature 1 markers in steps d) and e); and g) identifying a difference between the first difference and the second difference, wherein the difference identified in g) is indicative of the progression or regression of said prostate cancer in the subject.

6. A method for identifying a compound capable of ameliorating or treating prostate cancer in a subject comprising:

a) measuring the levels of one or more markers selected from the group consisting of Signature 1 markers in a population of the subject's macrophage cells before administering the compound to the subject;

b) measuring the levels of the one or more selected Signature 1 markers in a population of the subject's non-phagocytic cells before administering the compound to the subject;

c) identifying a first difference between the measured levels of the one or more selected Signature 1 markers in steps a) and b);

d) measuring the levels of the one or more selected Signature 1 markers in a population of the subject's macrophage cells after the administration of the compound;

e) measuring the levels of the one or more selected Signature 1 markers in a population of the subject's non-phagocytic cells after the administration of the compound;

f) identifying a second difference between the measured levels of the one or more selected Signature 1 markers in steps d) and e); and g) identifying a difference between the first difference and the second difference, wherein the difference identified in g) indicates that the compound is capable of ameliorating or treating said prostate cancer in the subject.

7. A method for diagnosing or aiding in the diagnosis of prostate cancer in a subject, the method comprising the steps of:

a) measuring the levels of one or more markers selected from the group consisting of Signature 2 markers in a population of the subject's macrophage cells;

b) measuring the levels of the one or more selected Signature 2 markers in a population of the subject's non-phagocytic cells; and c) identifying a difference between the measured levels of the one or more selected Signature 2 markers in steps a) and b), wherein the identified difference indicates that the subject has said prostate cancer.

8. A method for assessing the risk of developing prostate cancer in a subject, the method comprising the steps of:

a) measuring the levels of one or more markers selected from the group consisting of Signature 2 markers in a population of the subject's macrophage cells;

b) measuring the levels of the one or more selected Signature 2 markers in a population of the subject's non-phagocytic cells; and c) identifying a difference between the measured levels of the one or more selected Signature 2 markers in steps a) and b), wherein the identified difference indicates that the subject has a risk of developing said prostate cancer.

9. A method for prognosing or aiding in the prognosis of prostate cancer in a subject, the method comprising the steps of:

a) measuring the levels of one or more markers selected from the group consisting of Signature 2 markers in a population of the subject's macrophage cells;

b) measuring the levels of the one or more selected Signature 2 markers in a population of the subject's non-phagocytic cells; and c) identifying a difference between the measured levels of the one or more selected Signature 2 markers in steps a) and b), wherein the identified difference is indicative of the prognosis of said prostate cancer in the subject.

10. A method for assessing the efficacy of a treatment for prostate cancer in a subject comprising:

a) measuring the levels of one or more markers selected from the group consisting of Signature 2 markers in a population of the subject's macrophage cells before the treatment;

b) measuring the levels of the one or more selected Signature 2 markers in a population of the subject's non-phagocytic cells before the treatment;

c) identifying a first difference between the measured levels of the one or more selected Signature 2 markers in steps a) and b);

d) measuring the levels of the one or more selected Signature 2 markers in a population of the subject's macrophage cells after the treatment;

e) measuring the levels of the one or more selected Signature 2 markers in a population of the subject's non-phagocytic cells after the treatment;

f) identifying a second difference between the measured levels of the one or more selected Signature 2 markers in steps d) and e); and g) identifying a difference between the first difference and the second difference, wherein the difference identified in g) is indicative of the efficacy of the treatment for said prostate cancer in the subject.

11. A method for monitoring the progression or regression of prostate cancer in a subject comprising:

a) measuring the levels of one or more markers selected from the group consisting of Signature 2 markers in a population of the subject's macrophage cells at a first time point;

b) measuring the levels of the one or more selected Signature 2 markers in a population of the subject's non-phagocytic cells at the first time point;

c) identifying a first difference between the measured levels of the one or more selected Signature 2 markers in steps a) and b);

d) measuring the levels of the one or more selected Signature 2 markers in a population of the subject's macrophage cells at a second time point;

e) measuring the levels of the one or more selected Signature 2 markers in a population of the subject's non-phagocytic cells at the second time point;

f) identifying a second difference between the measured levels of the one or more selected Signature 2 markers in steps d) and e); and g) identifying a difference between the first difference and the second difference, wherein the difference identified in g) is indicative of the progression or regression of said prostate cancer in the subject.

12. A method for identifying a compound capable of ameliorating or treating prostate cancer in a subject comprising:

a) measuring the levels of one or more markers selected from the group consisting of Signature 2 markers in a population of the subject's macrophage cells before administering the compound to the subject;

b) measuring the levels of the one or more selected Signature 2 markers in a population of the subject's non-phagocytic cells before administering the compound to the subject;

c) identifying a first difference between the measured levels of the one or more selected Signature 2 markers in steps a) and b);

d) measuring the levels of the one or more selected Signature 2 markers in a population of the subject's macrophage cells after the administration of the compound;

e) measuring the levels of the one or more selected Signature 2 markers in a population of the subject's non-phagocytic cells after the administration of the compound;

f) identifying a second difference between the measured levels of the one or more selected Signature 2 markers in steps d) and e); and g) identifying a difference between the first difference and the second difference, wherein the difference identified in g) indicates that the compound is capable of ameliorating or treating said prostate cancer in the subject.

13. A method for diagnosing or aiding in the diagnosis of prostate cancer in a subject, the method comprising the steps of:

a) measuring the levels of one or more markers selected from the group consisting of Signature 3 markers in a population of the subject's macrophage cells;

b) measuring the levels of the one or more selected Signature 3 markers in a population of the subject's non-phagocytic cells; and c) identifying a difference between the measured levels of the one or more selected Signature 3 markers in steps a) and b), wherein the identified difference indicates that the subject has said prostate cancer.

14. A method for assessing the risk of developing prostate cancer in a subject, the method comprising the steps of:

a) measuring the levels of one or more markers selected from the group consisting of Signature 3 markers in a population of the subject's macrophage cells;

b) measuring the levels of the one or more selected Signature 3 markers in a population of the subject's non-phagocytic cells; and c) identifying a difference between the measured levels of the one or more selected Signature 3 markers in steps a) and b), wherein the identified difference indicates that the subject has a risk of developing said prostate cancer.

15. A method for prognosing or aiding in the prognosis of prostate cancer in a subject, the method comprising the steps of:

a) measuring the levels of one or more markers selected from the group consisting of Signature 3 markers in a population of the subject's macrophage cells;

b) measuring the levels of the one or more selected Signature 3 markers in a population of the subject's non-phagocytic cells; and c) identifying a difference between the measured levels of the one or more selected Signature 3 markers in steps a) and b), wherein the identified difference is indicative of the prognosis of said prostate cancer in the subject.

16. A method for assessing the efficacy of a treatment for prostate cancer in a subject comprising:

a) measuring the levels of one or more markers selected from the group consisting of Signature 3 markers in a population of the subject's macrophage cells before the treatment;

b) measuring the levels of the one or more selected Signature 3 markers in a population of the subject's non-phagocytic cells before the treatment;

c) identifying a first difference between the measured levels of the one or more selected Signature 3 markers in steps a) and b);

d) measuring the levels of the one or more selected Signature 3 markers in a population of the subject's macrophage cells after the treatment;

e) measuring the levels of the one or more selected Signature 3 markers in a population of the subject's non-phagocytic cells after the treatment;

f) identifying a second difference between the measured levels of the one or more selected Signature 3 markers in steps d) and e); and g) identifying a difference between the first difference and the second difference, wherein the difference identified in g) is indicative of the efficacy of the treatment for said prostate cancer in the subject.

17. A method for monitoring the progression or regression of prostate cancer in a subject comprising:

a) measuring the levels of one or more markers selected from the group consisting of Signature 3 markers in a population of the subject's macrophage cells at a first time point;

b) measuring the levels of the one or more selected Signature 3 markers in a population of the subject's non-phagocytic cells at the first time point;

c) identifying a first difference between the measured levels of the one or more selected Signature 3 markers in steps a) and b);

d) measuring the levels of the one or more selected Signature 3 markers in a population of the subject's macrophage cells at a second time point;

e) measuring the levels of the one or more selected Signature 3 markers in a population of the subject's non-phagocytic cells at the second time point;

f) identifying a second difference between the measured levels of the one or more selected Signature 3 markers in steps d) and e); and g) identifying a difference between the first difference and the second difference, wherein the difference identified in g) is indicative of the progression or regression of said prostate cancer in the subject.

18. A method for identifying a compound capable of ameliorating or treating prostate cancer in a subject comprising:

a) measuring the levels of one or more markers selected from the group consisting of Signature 3 markers in a population of the subject's macrophage cells before administering the compound to the subject;

b) measuring the levels of the one or more selected Signature 3 markers in a population of the subject's non-phagocytic cells before administering the compound to the subject;

c) identifying a first difference between the measured levels of the one or more selected Signature 3 markers in steps a) and b);

d) measuring the levels of the one or more selected Signature 3 markers in a population of the subject's macrophage cells after the administration of the compound;

e) measuring the levels of the one or more selected Signature 3 markers in a population of the subject's non-phagocytic cells after the administration of the compound;

f) identifying a second difference between the measured levels of the one or more selected Signature 3 markers in steps d) and e); and g) identifying a difference between the first difference and the second difference, wherein the difference identified in g) indicates that the compound is capable of ameliorating or treating said prostate cancer in the subject.

19. A method for diagnosing or aiding in the diagnosis of prostate cancer in a subject, the method comprising the steps of:

a) measuring the levels of one or more markers selected from the group consisting of Signature 4 markers in a population of the subject's macrophage cells;

b) measuring the levels of the one or more selected Signature 4 markers in a population of the subject's non-phagocytic cells; and c) identifying a difference between the measured levels of the one or more selected Signature 4 markers in steps a) and b), wherein the identified difference indicates that the subject has said prostate cancer.

20. A method for assessing the risk of developing prostate cancer in a subject, the method comprising the steps of:

a) measuring the levels of one or more markers selected from the group consisting of Signature 4 markers in a population of the subject's macrophage cells;

b) measuring the levels of the one or more selected Signature 4 markers in a population of the subject's non-phagocytic cells; and c) identifying a difference between the measured levels of the one or more selected Signature 4 markers in steps a) and b), wherein the identified difference indicates that the subject has a risk of developing said prostate cancer.

21. A method for prognosing or aiding in the prognosis of prostate cancer in a subject, the method comprising the steps of:

a) measuring the levels of one or more markers selected from the group consisting of Signature 4 markers in a population of the subject's macrophage cells;

b) measuring the levels of the one or more selected Signature 4 markers in a population of the subject's non-phagocytic cells; and c) identifying a difference between the measured levels of the one or more selected Signature 4 markers in steps a) and b), wherein the identified difference is indicative of the prognosis of said prostate cancer in the subject.

22. A method for assessing the efficacy of a treatment for prostate cancer in a subject comprising:

a) measuring the levels of one or more markers selected from the group consisting of Signature 4 markers in a population of the subject's macrophage cells before the treatment;

b) measuring the levels of the one or more selected Signature 4 markers in a population of the subject's non-phagocytic cells before the treatment;

c) identifying a first difference between the measured levels of the one or more selected Signature 4 markers in steps a) and b);

d) measuring the levels of the one or more selected Signature 4 markers in a population of the subject's macrophage cells after the treatment;

e) measuring the levels of the one or more selected Signature 4 markers in a population of the subject's non-phagocytic cells after the treatment;

f) identifying a second difference between the measured levels of the one or more selected Signature 4 markers in steps d) and e); and g) identifying a difference between the first difference and the second difference, wherein the difference identified in g) is indicative of the efficacy of the treatment for said prostate cancer in the subject.

23. A method for monitoring the progression or regression of prostate cancer in a subject comprising:

a) measuring the levels of one or more markers selected from the group consisting of Signature 4 markers in a population of the subject's macrophage cells at a first time point;

b) measuring the levels of the one or more selected Signature 4 markers in a population of the subject's non-phagocytic cells at the first time point;

c) identifying a first difference between the measured levels of the one or more selected Signature 4 markers in steps a) and b);

d) measuring the levels of the one or more selected Signature 4 markers in a population of the subject's macrophage cells at a second time point;

e) measuring the levels of the one or more selected Signature 4 markers in a population of the subject's non-phagocytic cells at the second time point;

f) identifying a second difference between the measured levels of the one or more selected Signature 4 markers in steps d) and e); and g) identifying a difference between the first difference and the second difference, wherein the difference identified in g) is indicative of the progression or regression of said prostate cancer in the subject.

24. A method for identifying a compound capable of ameliorating or treating prostate cancer in a subject comprising:

a) measuring the levels of one or more markers selected from the group consisting of Signature 4 markers in a population of the subject's macrophage cells before administering the compound to the subject;

b) measuring the levels of the one or more selected Signature 4 markers in a population of the subject's non-phagocytic cells before administering the compound to the subject;

c) identifying a first difference between the measured levels of the one or more selected Signature 4 markers in steps a) and b);

d) measuring the levels of the one or more selected Signature 4 markers in a population of the subject's macrophage cells after the administration of the compound;

e) measuring the levels of the one or more selected Signature 4 markers in a population of the subject's non-phagocytic cells after the administration of the compound;

f) identifying a second difference between the measured levels of the one or more selected Signature 4 markers in steps d) and e); and g) identifying a difference between the first difference and the second difference, wherein the difference identified in g) indicates that the compound is capable of ameliorating or treating said prostate cancer in the subject.

25. A method for diagnosing or aiding in the diagnosis of prostate cancer in a subject, the method comprising the steps of:

a) measuring the levels of one or more markers selected from the group consisting of Signature 1 markers in a population of the subject's neutrophil cells;

b) measuring the levels of the one or more selected Signature 1 markers in a population of the subject's non-phagocytic cells; and c) identifying a difference between the measured levels of the one or more selected Signature 1 markers in steps a) and b), wherein the identified difference indicates that the subject has said prostate cancer.

26. A method for assessing the risk of developing prostate cancer in a subject, the method comprising the steps of:

a) measuring the levels of one or more markers selected from the group consisting of Signature 1 markers in a population of the subject's neutrophil cells;

b) measuring the levels of the one or more selected Signature 1 markers in a population of the subject's non-phagocytic cells; and c) identifying a difference between the measured levels of the one or more selected Signature 1 markers in steps a) and b), wherein the identified difference indicates that the subject has a risk of developing said prostate cancer.

27. A method for prognosing or aiding in the prognosis of prostate cancer in a subject, the method comprising the steps of:

a) measuring the levels of one or more markers selected from the group consisting of Signature 1 markers in a population of the subject's neutrophil cells;

b) measuring the levels of the one or more selected Signature 1 markers in a population of the subject's non-phagocytic cells; and c) identifying a difference between the measured levels of the one or more selected Signature 1 markers in steps a) and b), wherein the identified difference is indicative of the prognosis of said prostate cancer in the subject.

28. A method for assessing the efficacy of a treatment for prostate cancer in a subject comprising:

a) measuring the levels of one or more markers selected from the group consisting of Signature 1 markers in a population of the subject's neutrophil cells before the treatment;

b) measuring the levels of the one or more selected Signature 1 markers in a population of the subject's non-phagocytic cells before the treatment;

c) identifying a first difference between the measured levels of the one or more selected Signature 1 markers in steps a) and b);

d) measuring the levels of the one or more selected Signature 1 markers in a population of the subject's neutrophil cells after the treatment;

e) measuring the levels of the one or more selected Signature 1 markers in a population of the subject's non-phagocytic cells after the treatment;

f) identifying a second difference between the measured levels of the one or more selected Signature 1 markers in steps d) and e); and g) identifying a difference between the first difference and the second difference, wherein the difference identified in g) is indicative of the efficacy of the treatment for said prostate cancer in the subject.

29. A method for monitoring the progression or regression of prostate cancer in a subject comprising:

a) measuring the levels of one or more markers selected from the group consisting of Signature 1 markers in a population of the subject's neutrophil cells at a first time point;

b) measuring the levels of the one or more selected Signature 1 markers in a population of the subject's non-phagocytic cells at the first time point;

c) identifying a first difference between the measured levels of the one or more selected Signature 1 markers in steps a) and b);

d) measuring the levels of the one or more selected Signature 1 markers in a population of the subject's neutrophil cells at a second time point;

e) measuring the levels of the one or more selected Signature 1 markers in a population of the subject's non-phagocytic cells at the second time point;

f) identifying a second difference between the measured levels of the one or more selected Signature 1 markers in steps d) and e); and g) identifying a difference between the first difference and the second difference, wherein the difference identified in g) is indicative of the progression or regression of said prostate cancer in the subject.

30. A method for identifying a compound capable of ameliorating or treating prostate cancer in a subject comprising:

a) measuring the levels of one or more markers selected from the group consisting of Signature 1 markers in a population of the subject's neutrophil cells before administering the compound to the subject;

b) measuring the levels of the one or more selected Signature 1 markers in a population of the subject's non-phagocytic cells before administering the compound to the subject;

c) identifying a first difference between the measured levels of the one or more selected Signature 1 markers in steps a) and b);

d) measuring the levels of the one or more selected Signature 1 markers in a population of the subject's neutrophil cells after the administration of the compound;

e) measuring the levels of the one or more selected Signature 1 markers in a population of the subject's non-phagocytic cells after the administration of the compound;

f) identifying a second difference between the measured levels of the one or more selected Signature 1 markers in steps d) and e); and g) identifying a difference between the first difference and the second difference, wherein the difference identified in g) indicates that the compound is capable of ameliorating or treating said prostate cancer in the subject.

31. A method for diagnosing or aiding in the diagnosis of prostate cancer in a subject, the method comprising the steps of:

a) measuring the levels of one or more markers selected from the group consisting of Signature 2 markers in a population of the subject's neutrophil cells;

b) measuring the levels of the one or more selected Signature 2 markers in a population of the subject's non-phagocytic cells; and c) identifying a difference between the measured levels of the one or more selected Signature 2 markers in steps a) and b), wherein the identified difference indicates that the subject has said prostate cancer.

32. A method for assessing the risk of developing prostate cancer in a subject, the method comprising the steps of:

a) measuring the levels of one or more markers selected from the group consisting of Signature 2 markers in a population of the subject's neutrophil cells;

b) measuring the levels of the one or more selected Signature 2 markers in a population of the subject's non-phagocytic cells; and c) identifying a difference between the measured levels of the one or more selected Signature 2 markers in steps a) and b), wherein the identified difference indicates that the subject has a risk of developing said prostate cancer.

33. A method for prognosing or aiding in the prognosis of prostate cancer in a subject, the method comprising the steps of:

a) measuring the levels of one or more markers selected from the group consisting of Signature 2 markers in a population of the subject's neutrophil cells;

b) measuring the levels of the one or more selected Signature 2 markers in a population of the subject's non-phagocytic cells; and c) identifying a difference between the measured levels of the one or more selected Signature 2 markers in steps a) and b), wherein the identified difference is indicative of the prognosis of said prostate cancer in the subject.

34. A method for assessing the efficacy of a treatment for prostate cancer in a subject comprising:

a) measuring the levels of one or more markers selected from the group consisting of Signature 2 markers in a population of the subject's neutrophil cells before the treatment;

b) measuring the levels of the one or more selected Signature 2 markers in a population of the subject's non-phagocytic cells before the treatment;

c) identifying a first difference between the measured levels of the one or more selected Signature 2 markers in steps a) and b);

d) measuring the levels of the one or more selected Signature 2 markers in a population of the subject's neutrophil cells after the treatment;

e) measuring the levels of the one or more selected Signature 2 markers in a population of the subject's non-phagocytic cells after the treatment;

f) identifying a second difference between the measured levels of the one or more selected Signature 2 markers in steps d) and e); and g) identifying a difference between the first difference and the second difference, wherein the difference identified in g) is indicative of the efficacy of the treatment for said prostate cancer in the subject.

35. A method for monitoring the progression or regression of prostate cancer in a subject comprising:

a) measuring the levels of one or more markers selected from the group consisting of Signature 2 markers in a population of the subject's neutrophil cells at a first time point;

b) measuring the levels of the one or more selected Signature 2 markers in a population of the subject's non-phagocytic cells at the first time point;

c) identifying a first difference between the measured levels of the one or more selected Signature 2 markers in steps a) and b);

d) measuring the levels of the one or more selected Signature 2 markers in a population of the subject's neutrophil cells at a second time point;

e) measuring the levels of the one or more selected Signature 2 markers in a population of the subject's non-phagocytic cells at the second time point;

f) identifying a second difference between the measured levels of the one or more selected Signature 2 markers in steps d) and e); and g) identifying a difference between the first difference and the second difference, wherein the difference identified in g) is indicative of the progression or regression of said prostate cancer in the subject.

36. A method for identifying a compound capable of ameliorating or treating prostate cancer in a subject comprising:

a) measuring the levels of one or more markers selected from the group consisting of Signature 2 markers in a population of the subject's neutrophil cells before administering the compound to the subject;

b) measuring the levels of the one or more selected Signature 2 markers in a population of the subject's non-phagocytic cells before administering the compound to the subject;

c) identifying a first difference between the measured levels of the one or more selected Signature 2 markers in steps a) and b);

d) measuring the levels of the one or more selected Signature 2 markers in a population of the subject's neutrophil cells after the administration of the compound;

e) measuring the levels of the one or more selected Signature 2 markers in a population of the subject's non-phagocytic cells after the administration of the compound;

f) identifying a second difference between the measured levels of the one or more selected Signature 2 markers in steps d) and e); and g) identifying a difference between the first difference and the second difference, wherein the difference identified in g) indicates that the compound is capable of ameliorating or treating said prostate cancer in the subject.

37. A method for diagnosing or aiding in the diagnosis of prostate cancer in a subject, the method comprising the steps of:

a) measuring the levels of one or more markers selected from the group consisting of Signature 3 markers in a population of the subject's neutrophil cells;

b) measuring the levels of the one or more selected Signature 3 markers in a population of the subject's non-phagocytic cells; and c) identifying a difference between the measured levels of the one or more selected Signature 3 markers in steps a) and b), wherein the identified difference indicates that the subject has said prostate cancer.

38. A method for assessing the risk of developing prostate cancer in a subject, the method comprising the steps of:

a) measuring the levels of one or more markers selected from the group consisting of Signature 3 markers in a population of the subject's neutrophil cells;

b) measuring the levels of the one or more selected Signature 3 markers in a population of the subject's non-phagocytic cells; and c) identifying a difference between the measured levels of the one or more selected Signature 3 markers in steps a) and b), wherein the identified difference indicates that the subject has a risk of developing said prostate cancer.

39. A method for prognosing or aiding in the prognosis of prostate cancer in a subject, the method comprising the steps of:

a) measuring the levels of one or more markers selected from the group consisting of Signature 3 markers in a population of the subject's neutrophil cells;

b) measuring the levels of the one or more selected Signature 3 markers in a population of the subject's non-phagocytic cells; and c) identifying a difference between the measured levels of the one or more selected Signature 3 markers in steps a) and b), wherein the identified difference is indicative of the prognosis of said prostate cancer in the subject.

40. A method for assessing the efficacy of a treatment for prostate cancer in a subject comprising:

a) measuring the levels of one or more markers selected from the group consisting of Signature 3 markers in a population of the subject's neutrophil cells before the treatment;

b) measuring the levels of the one or more selected Signature 3 markers in a population of the subject's non-phagocytic cells before the treatment;

c) identifying a first difference between the measured levels of the one or more selected Signature 3 markers in steps a) and b);

d) measuring the levels of the one or more selected Signature 3 markers in a population of the subject's neutrophil cells after the treatment;

e) measuring the levels of the one or more selected Signature 3 markers in a population of the subject's non-phagocytic cells after the treatment;

f) identifying a second difference between the measured levels of the one or more selected Signature 3 markers in steps d) and e); and g) identifying a difference between the first difference and the second difference, wherein the difference identified in g) is indicative of the efficacy of the treatment for said prostate cancer in the subject.

41. A method for monitoring the progression or regression of prostate cancer in a subject comprising:

a) measuring the levels of one or more markers selected from the group consisting of Signature 3 markers in a population of the subject's neutrophil cells at a first time point;

b) measuring the levels of the one or more selected Signature 3 markers in a population of the subject's non-phagocytic cells at the first time point;

c) identifying a first difference between the measured levels of the one or more selected Signature 3 markers in steps a) and b);

d) measuring the levels of the one or more selected Signature 3 markers in a population of the subject's neutrophil cells at a second time point;

e) measuring the levels of the one or more selected Signature 3 markers in a population of the subject's non-phagocytic cells at the second time point;

f) identifying a second difference between the measured levels of the one or more selected Signature 3 markers in steps d) and e); and g) identifying a difference between the first difference and the second difference, wherein the difference identified in g) is indicative of the progression or regression of said prostate cancer in the subject.

42. A method for identifying a compound capable of ameliorating or treating prostate cancer in a subject comprising:

a) measuring the levels of one or more markers selected from the group consisting of Signature 3 markers in a population of the subject's neutrophil cells before administering the compound to the subject;

b) measuring the levels of the one or more selected Signature 3 markers in a population of the subject's non-phagocytic cells before administering the compound to the subject;

c) identifying a first difference between the measured levels of the one or more selected Signature 3 markers in steps a) and b);

d) measuring the levels of the one or more selected Signature 3 markers in a population of the subject's neutrophil cells after the administration of the compound;

e) measuring the levels of the one or more selected Signature 3 markers in a population of the subject's non-phagocytic cells after the administration of the compound;

f) identifying a second difference between the measured levels of the one or more selected Signature 3 markers in steps d) and e); and g) identifying a difference between the first difference and the second difference, wherein the difference identified in g) indicates that the compound is capable of ameliorating or treating said prostate cancer in the subject.

43. A method for diagnosing or aiding in the diagnosis of prostate cancer in a subject, the method comprising the steps of:

a) measuring the levels of one or more markers selected from the group consisting of Signature 4 markers in a population of the subject's neutrophil cells;

b) measuring the levels of the one or more selected Signature 4 markers in a population of the subject's non-phagocytic cells; and c) identifying a difference between the measured levels of the one or more selected Signature 4 markers in steps a) and b), wherein the identified difference indicates that the subject has said prostate cancer.

44. A method for assessing the risk of developing prostate cancer in a subject, the method comprising the steps of:

a) measuring the levels of one or more markers selected from the group consisting of Signature 4 markers in a population of the subject's neutrophil cells;

b) measuring the levels of the one or more selected Signature 4 markers in a population of the subject's non-phagocytic cells; and c) identifying a difference between the measured levels of the one or more selected Signature 4 markers in steps a) and b), wherein the identified difference indicates that the subject has a risk of developing said prostate cancer.

45. A method for prognosing or aiding in the prognosis of prostate cancer in a subject, the method comprising the steps of:

a) measuring the levels of one or more markers selected from the group consisting of Signature 4 markers in a population of the subject's neutrophil cells;

b) measuring the levels of the one or more selected Signature 4 markers in a population of the subject's non-phagocytic cells; and c) identifying a difference between the measured levels of the one or more selected Signature 4 markers in steps a) and b), wherein the identified difference is indicative of the prognosis of said prostate cancer in the subject.

46. A method for assessing the efficacy of a treatment for prostate cancer in a subject comprising:

a) measuring the levels of one or more markers selected from the group consisting of Signature 4 markers in a population of the subject's neutrophil cells before the treatment;

b) measuring the levels of the one or more selected Signature 4 markers in a population of the subject's non-phagocytic cells before the treatment;

c) identifying a first difference between the measured levels of the one or more selected Signature 4 markers in steps a) and b);

d) measuring the levels of the one or more selected Signature 4 markers in a population of the subject's neutrophil cells after the treatment;

e) measuring the levels of the one or more selected Signature 4 markers in a population of the subject's non-phagocytic cells after the treatment;

f) identifying a second difference between the measured levels of the one or more selected Signature 4 markers in steps d) and e); and g) identifying a difference between the first difference and the second difference, wherein the difference identified in g) is indicative of the efficacy of the treatment for said prostate cancer in the subject.

47. A method for monitoring the progression or regression of prostate cancer in a subject comprising:

a) measuring the levels of one or more markers selected from the group consisting of Signature 4 markers in a population of the subject's neutrophil cells at a first time point;

b) measuring the levels of the one or more selected Signature 4 markers in a population of the subject's non-phagocytic cells at the first time point;

c) identifying a first difference between the measured levels of the one or more selected Signature 4 markers in steps a) and b);

d) measuring the levels of the one or more selected Signature 4 markers in a population of the subject's neutrophil cells at a second time point;

e) measuring the levels of the one or more selected Signature 4 markers in a population of the subject's non-phagocytic cells at the second time point;

f) identifying a second difference between the measured levels of the one or more selected Signature 4 markers in steps d) and e); and g) identifying a difference between the first difference and the second difference, wherein the difference identified in g) is indicative of the progression or regression of said prostate cancer in the subject.

48. A method for identifying a compound capable of ameliorating or treating prostate cancer in a subject comprising:

a) measuring the levels of one or more markers selected from the group consisting of Signature 4 markers in a population of the subject's neutrophil cells before administering the compound to the subject;

b) measuring the levels of the one or more selected Signature 4 markers in a population of the subject's non-phagocytic cells before administering the compound to the subject;

c) identifying a first difference between the measured levels of the one or more selected Signature 4 markers in steps a) and b);

d) measuring the levels of the one or more selected Signature 4 markers in a population of the subject's neutrophil cells after the administration of the compound;

e) measuring the levels of the one or more selected Signature 4 markers in a population of the subject's non-phagocytic cells after the administration of the compound;

f) identifying a second difference between the measured levels of the one or more selected Signature 4 markers in steps d) and e); and g) identifying a difference between the first difference and the second difference, wherein the difference identified in g) indicates that the compound is capable of ameliorating or treating said prostate cancer in the subject.

49. The method of any one of embodiments 1-48, further comprising measuring at least one standard parameter associated with said prostate cancer.

50. The method of embodiment 49, wherein the standard parameter is selected from the group consisting of tumor stage, tumor grade, tumor size, tumor visual characteristics, tumor growth, tumor thickness, tumor progression, tumor metastasis tumor distribution within the body, odor, molecular pathology, genomics, or tumor angiograms.

51. The method of any one of embodiments 1-24, wherein the selected Signature 1, Signature 2, Signature 3, or Signature 4 markers are up-regulated or activated in the macrophage cells compared to the non-phagocytic cells.

52. The method of any one of embodiments 1-24, wherein the selected Signature 1, Signature 2, Signature 3, or Signature 4 markers are down-regulated or inhibited in the macrophage cells compared to the non-phagocytic cells.

53. The method of any one of embodiments 1-24, wherein the selected Signature 1, Signature 2, Signature 3, or Signature 4 markers are up-regulated or activated in the neutrophil cells compared to the non-phagocytic cells.

54. The method of any one of embodiments 1-24, wherein the selected Signature 1, Signature 2, Signature 3, or Signature 4 markers are down-regulated or inhibited in the neutrophil cells compared to the non-phagocytic cells.

55. The method of any one of embodiments 1-6 or 25-30, wherein at least two, three, four, five, six, seven, eight, nine, ten, or eleven markers are selected from Signature 1.

56. The method of any one of embodiments 7-12 or 31-36, wherein at least two, three, four, five, six, seven, eight, nine, ten, or eleven markers are selected from Signature 2.

57. The method of any one of embodiments 13-18 or 37-42, wherein at least two, three, four, five, six, seven, eight, nine, ten, or eleven markers are selected from Signature 3.

58. The method of any one of embodiments 19-24 or 43-48, wherein at least two, three, four, five, six, seven, eight, nine, ten, or eleven markers are selected from Signature 4.

59. The method of any one of embodiments 1-24, further comprising lysing the macrophage cells and the non-phagocytic cells before a).

60. The method of any one of embodiments 1-24, further comprising extracting the cellular contents from the macrophage cells and the non-phagocytic cells before a).

61. The method of any one of embodiments 25-48, further comprising lysing the neutrophil cells and the non-phagocytic cells before a).

62. The method of any one of embodiments 25-48, further comprising extracting the cellular contents from the neutrophil cells and the non-phagocytic cells before a).

63. The method of embodiment 60, wherein the cellular contents of the macrophage cells comprise viable diseased cells, dead diseased cells, apoptotic diseased cells, circulating tumor cells, infectious agents, fetal cells, trophoblasts, or fragments thereof.

64. The method of embodiment 62, wherein the cellular contents of the neutrophil cells comprise viable diseased cells, dead diseased cells, apoptotic diseased cells, circulating tumor cells, infectious agents, fetal cells, trophoblasts, or fragments thereof.

65. The method of embodiment 60, wherein the selected one or more markers are present in the cellular contents of the macrophage cells.

66. The method of any one of embodiments 1-48, wherein the non-phagocytic cells are T cells, B cells, null cells, basophils, or mixtures thereof.

67. The method of any one of embodiments 1-24, wherein the macrophage cells are isolated from a bodily fluid sample, tissues, or cells of the subject.

68. The method of any one of embodiments 25-48, wherein the neutrophil cells are isolated from a bodily fluid sample, tissues, or cells of the subject.

69. The method of any one of embodiments 1-48, wherein the non-phagocytic cells are isolated from a bodily fluid sample, tissues, or cells of the subject.

70. The method of any one of embodiments 67-69, wherein the bodily fluid sample is blood, urine, stool, saliva, lymph fluid, cerebrospinal fluid, synovial fluid, cystic fluid, ascites, pleural effusion, fluid obtained from a pregnant woman in the first trimester, fluid obtained from a pregnant woman in the second trimester, fluid obtained from a pregnant woman in the third trimester, maternal blood, amniotic fluid, chorionic villus sample, fluid from a preimplantation embryo, maternal urine, maternal saliva, placental sample, fetal blood, lavage and cervical vaginal fluid, interstitial fluid, or ocular fluid.

71. The method of any one of embodiments 1-24, wherein the macrophage cells are isolated using antibodies, using a ligand that binds to a molecular receptor expressed on the plasma membranes of white blood cells, or by flow cytometry, fluorescence activated cell sorting, filtration, gradient-based centrifugation, elution, microfluidics, magnetic separation technique, fluorescent-magnetic separation technique, nanostructure, quantum dots, high throughput microscope-based platforms, or a combination thereof.

72. The method of any one of embodiments 25-48, wherein the neutrophil cells are isolated using antibodies, using a ligand that binds to a molecular receptor expressed on the plasma membranes of white blood cells, or by flow cytometry, fluorescence activated cell sorting, filtration, gradient-based centrifugation, elution, microfluidics, magnetic separation technique, fluorescent-magnetic separation technique, nanostructure, quantum dots, high throughput microscope-based platforms, or a combination thereof.

73. The method of any one of embodiments 1-48, wherein the non-phagocytic cells are isolated using antibodies, using a ligand that binds to a molecular receptor expressed on the plasma membranes of white blood cells, or by flow cytometry, fluorescence activated cell sorting, filtration, gradient-based centrifugation, elution, microfluidics, magnetic separation technique, fluorescent-magnetic separation technique, nanostructure, quantum dots, high throughput microscope-based platforms, or a combination thereof.

74. The method of any one of embodiments 1-24, wherein the macrophage cells are isolated using a product secreted by the macrophage cells.

75. The method of any one of embodiments 25-48, wherein the neutrophil cells are isolated by using a product secreted by the neutrophil cells.

76. The method of any one the embodiments 1-24, wherein the macrophage cells are isolated by using a cell surface target on the surface of macrophage cells.

77. The method of any one of embodiments 25-48, wherein the neutrophil cells are isolated by using a cell surface target on the surface of neutrophil cells.

78. The method of embodiment 76, wherein the target is expressed by the macrophage cells.

79. The method of embodiment 76, wherein the target is not expressed by the macrophage cells.

80. The method of embodiment 77, wherein the target is expressed by the neutrophil cells.

81. The method of embodiment 77, wherein the target is not expressed by the neutrophil cells.

82. The method of any one of embodiments 76-81, wherein the target is a marker of said prostate cancer.

83. The method of any one of embodiments 1-48, wherein the measured levels are gene expression levels.

84. The method of any one of embodiments 1-48, wherein the measured levels are protein expression levels.

85. The method of any one of the embodiment 1-48, wherein the levels or activities are measured by a qualitative assay, a quantitative assay, or a combination thereof.

86. The method of embodiment 85, wherein the quantitative assay uses sequencing, direct sequencing, RNA sequencing, whole transcriptome shotgun sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, matrix assisted laser desorption/ionization-time of flight (MALDI-TOF) mass spectrometry, electrospray ionization (ESI) mass spectrometry, surface-enhanced laser desorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), polymerase chain reaction (PCR) analysis, quantitative PCR, real-time PCR, fluorescence assay, colorimetric assay, chemiluminescent assay, or a combination thereof.

87. The method of embodiment 83, wherein the gene expression levels are measured by polymerase chain reaction (PCR) analysis, sequencing analysis, electrophoretic analysis, restriction fragment length polymorphism (RFLP) analysis, Northern blot analysis, quantitative PCR, reverse-transcriptase-PCR analysis (RT-PCR), allele-specific oligonucleotide hybridization analysis, comparative genomic hybridization, heteroduplex mobility assay (HMA), single strand conformational polymorphism (SSCP), denaturing gradient gel electrophisis (DGGE), RNAase mismatch analysis, mass spectrometry, tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), surface plasmon resonance, Southern blot analysis, in situ hybridization, fluorescence in situ hybridization (FISH), chromogenic in situ hybridization (CISH), immunohistochemistry (IHC), microarray, comparative genomic hybridization, karyotyping, multiplex ligation-dependent probe amplification (MLPA), Quantitative Multiplex PCR of Short Fluorescent Fragments (QMPSF), microscopy, methylation specific PCR (MSP) assay, HpaII tiny fragment Enrichment by Ligation-mediated PCR (HELP) assay, radioactive acetate labeling assays, colorimetric DNA acetylation assay, chromatin immunoprecipitation combined with microarray (ChIP-on-chip) assay, restriction landmark genomic scanning, Methylated DNA immunoprecipitation (MeDIP), molecular break light assay for DNA adenine methyltransferase activity, chromatographic separation, methylation-sensitive restriction enzyme analysis, bisulfite-driven conversion of non-methylated cytosine to uracil, methyl-binding PCR analysis, or a combination thereof.

88. The method of embodiment 83, wherein the gene expression levels are measured by a sequencing technique selected from the group consisting of direct sequencing, RNA sequencing, whole transcriptome shotgun sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, and a combination thereof.

89. The method of embodiment 84, wherein the protein expression levels are measured by an immunohistochemistry assay, an enzyme-linked immunosorbent assay (ELISA), in situ hybridization, chromatography, liquid chromatography, size exclusion chromatography, high performance liquid chromatography (HPLC), gas chromatography, mass spectrometry, tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), radioimmunoassays, microscopy, microfluidic chip-based assays, surface plasmon resonance, sequencing, Western blotting assay, or a combination thereof.

90. The method of any one the embodiments 1-89, wherein the subject is a mammal.

91. The method of embodiment 90, wherein the subject is a human.

92. The method of any one the embodiments 1-48, wherein the difference is greater than a 1-fold difference.

93. The method of embodiment 92, wherein the difference is at least 1.05-fold, 1.1-fold, 1.2-fold, 1.3-fold, 1.4-fold, 1.5-fold, 2-fold, 2.5-fold, 3-fold, 4-fold, 5-fold, 6-fold, 7-fold, 8-fold, 9-fold, or 10-fold difference.

94. A kit for measuring the levels of at least one or more markers selected from the group consisting of Signature 1 markers, comprising reagents for specifically measuring the levels of the selected Signature 1 marker.

95. A kit for measuring the levels of at least one or more markers selected from the group consisting of Signature 2 markers, comprising reagents for specifically measuring the levels of the selected Signature 2 marker.

96. A kit for measuring the levels of at least one or more markers selected from the group consisting of Signature 3 markers, comprising reagents for specifically measuring the levels of the selected Signature 3 marker.

97. A kit for measuring the levels of at least one or more markers selected from the group consisting of Signature 4 markers, comprising reagents for specifically measuring the levels of the selected Signature 4 marker.

98. The kit of any one of embodiments 95 and 96, wherein the reagents comprise one or more antibodies or fragments thereof, oligonucleotides, or aptamers.

99. A method of treating or preventing prostate cancer in a subject comprising administering to said subject an agent that modulates the activity or expression of at least one or more markers selected from the group consisting of Signature 1.

100. A method of treating or preventing prostate cancer in a subject comprising administering to said subject an agent that modulates the activity or expression of at least one or more markers selected from the group consisting of Signature 2.

101. A method of treating or preventing prostate cancer in a subject comprising administering to said subject an agent that modulates the activity or expression of at least one or more markers selected from the group consisting of Signature 3.

102. A method of treating or preventing prostate cancer in a subject comprising administering to said subject an agent that modulates the activity or expression of at least one or more markers selected from the group consisting of Signature 4.

103. The method of any one of embodiments 99-102, wherein the agent is a small molecule modulator, siRNA, or an antibody or fragment thereof.

DETAILED DESCRIPTION OF THE INVENTION

Figure 1:
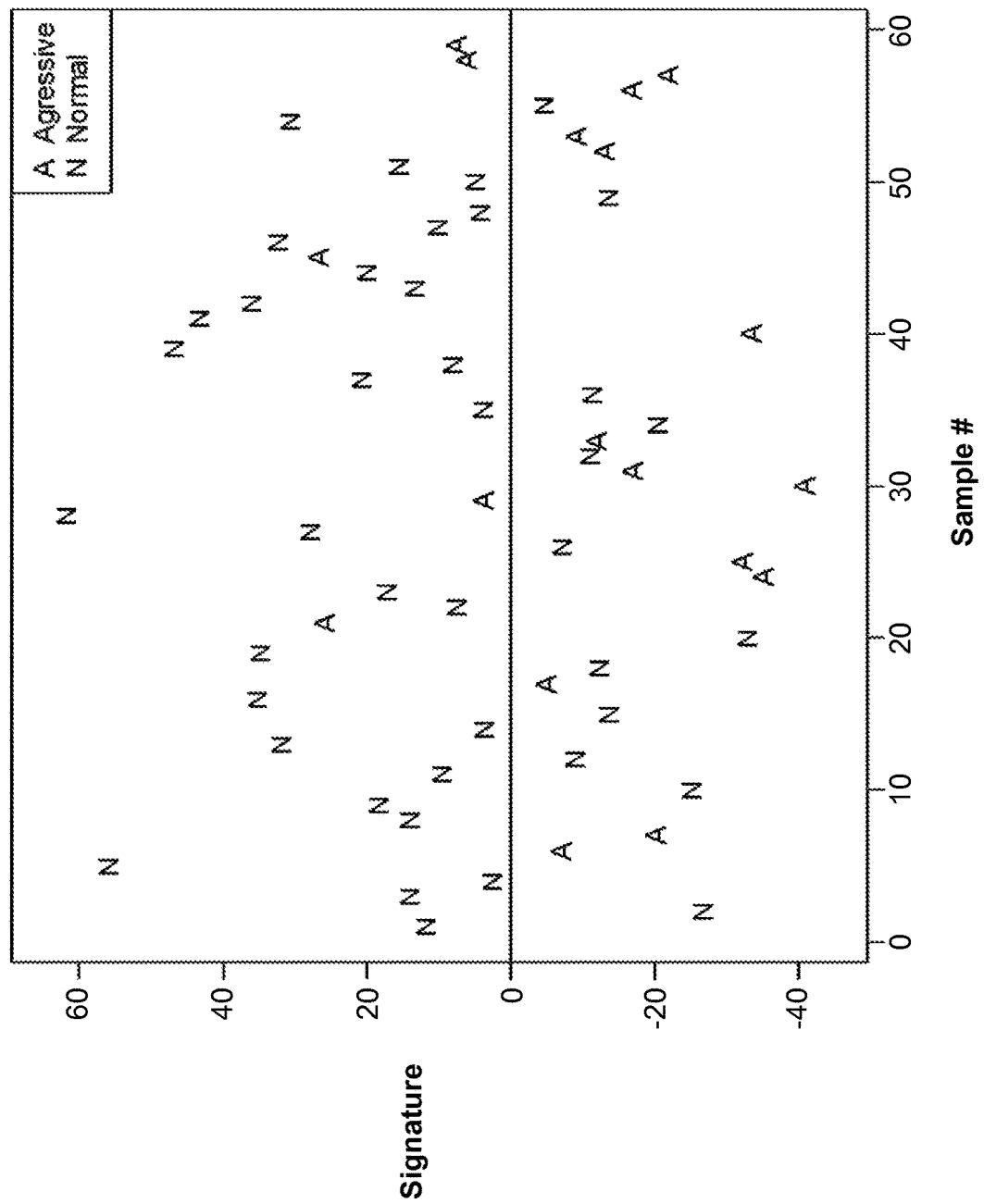
FIG. 1 depicts microarray results in a search for a signature of normal (N) vs. aggressive (A) cancer in subtraction-normalized expression data collected from blood samples processed 4 hours after collection.

The present invention provides biological markers and methods of using them to detect a cancer. More specifically, the present invention provides biomarkers that are specific for prostate cancer.

As used here in, a "biomarker" or "marker" refers to an analyte (e.g., a nucleic acid, DNA, RNA, peptide, protein, or metabolite) that can be objectively measured and evaluated as an indicator for a biological process. In some embodiments, a marker is differentially detectable in phagocytes and is indicative of the presence or absence of prostate cancer. An analyte is differentially detectable if it can be distinguished quantitatively or qualitatively in phagocytes compared to a control, e.g., a normal or healthy control or non-phagocytic cells.

The present invention is based on the discovery that one or more markers selected from Tables 1 and/or 2 and/or 3 and/or 4 (Signature 1 and/or Signature 2 and/or Signature 3 and/or Signature 4 markers, respectively) are useful in diagnosing prostate cancer. By measuring the levels of the biomarkers (e.g., gene expression levels, protein expression levels, or protein activity levels) in a population of phagocytes (e.g., macrophage or neutrophils) from a human subject, one can provide a reliable diagnosis for prostate cancer.

As used herein, a "level" of a marker of this invention can be qualitative (e.g., presence or absence) or quantitative (e.g., amounts, copy numbers, or dosages). In some embodiments, a level of a marker at a zero value can indicate the absence of this marker. The levels of any marker of this invention can be measured in various forms. For example, the level can be a gene expression level, a RNA transcript level, a protein expression level, a protein activity level, an enzymatic activity level.

The markers of this invention can be used in methods for diagnosing or aiding in the diagnosis of prostate cancer by comparing levels (e.g., gene expression levels, or protein expression levels, or protein activities) of one or more prostate cancer markers (e.g., nucleic acids or proteins) between phagocytes (e.g., macrophages or neutrophils) and non-phagocytic cells taken from the same individual. This invention also provides methods for assessing the risk of developing prostate cancer, prognosing said cancer, monitoring said cancer progression or regression, assessing the efficacy of a treatment, or identifying a compound capable of ameliorating or treating said cancer.

The methods of this invention can be applied to prostate cancer. As used herein, "prostate cancer" means any cancer of the prostate including, but not limited to, adenocarcinoma and small cell carcinoma.

In a first aspect, the methods (e.g., diagnosis of prostate cancer, prognosis of prostate cancer, or assessing the risk of developing prostate cancer) provided in the invention comprise: a) measuring the levels of one or more markers selected from Tables 1 and/or 2 and/or 3 and/or 4 (Signature 1 markers and/or Signature 2 markers and/or Signature 3 markers and/or Signature 4 markers, respectively) in a population of a subject's macrophage cells; b) measuring the levels of one or more of the selected markers in a population of a subject's non-phagocytic cells (e.g., T-cells, B-cells, null cells, basophils or the mixtures of two more non-phagocytic cells); comparing the measured levels in step a) to the measured levels in step b) and further identify a difference between the measured levels of a) and b). The identified difference is indicative of the diagnosis (e.g., presence or absence), prognosis (e.g., lethal outcome, or tumor stage), or the risk of developing prostate cancer.

In the first aspect, the selected markers comprise one or more (e.g., two, three, four, five, six, seven, eight, nine, ten, twenty, thirty, forty, fifty, one-hundred, one-hundred seventeen, or any increment between those values) markers of Signature 1, or one or more (e.g., two, three, four, five, six, seven, eight, nine, ten, eleven, twelve, thirteen, fourteen, fifteen, sixteen, seventeen, or eighteen) markers of Signature 2, or one or more (e.g., two, two, three, four, five, six, seven, eight, nine, ten, eleven, twelve, thirteen, fourteen, fifteen, sixteen, seventeen, or eighteen) markers of Signature 3, or one or more (e.g., two, two, three, four, five, six, seven, eight, nine, or ten) markers of Signature 4. In some embodiments, the selected markers are up-regulated (see Tables 1 and/or 2 and/or 3 and/or 4 for up-regulated markers) in prostate cancer patients. In some embodiments, the selected markers are down-regulated (see Table 1 for down-regulated markers) in prostate cancer patients. In some embodiments, the selected markers comprise at least one Signature 1 marker that is up-regulated and at least one Signature 1 marker that is down-regulated.

In a second aspect, the methods provided in this invention for assessing the efficacy of a treatment for prostate cancer, monitoring the progression or regression of prostate cancer, or identifying a compound capable of ameliorating or treating prostate cancer, respectively, in a subject comprising: a) measuring the levels of one or more markers selected from the group consisting of Signature 1 and/or Signature 2 and/or Signature 3 and/or Signature 4 (Tables 1 and/or 2 and/or 3 and/or 4, respectively) in a population of the subject's macrophage cells before the treatment, or at a first time point, or before administration of the compound, respectively; b) measuring the levels of the one or more selected Signature 1 and/or Signature 2 and/or Signature 3 and/or Signature 4 markers in a population of the subject's non-phagocytic cells before the treatment, or at the first time point, or before administration of the compound, respectively; c) identifying a first difference between the measured levels of the one or more selected Signature 1 and/or Signature 2 and/or Signature 3 and/or Signature 4 markers in steps a) and b); d) measuring the levels of the one or more selected Signature 1 and/or Signature 2 and/or Signature 3 and/or Signature 4 markers in a population of the subject's macrophage cells after the treatment, or at a second time point, or after administration of the compound, respectively; e) measuring the levels of the one or more selected Signature 1 and/or Signature 2 and/or Signature 3 and/or Signature 4 markers in a population of the subject's non-phagocytic cells after the treatment, or at the second time point, or after administration of the compound, respectively; f) identifying a second difference between the measured levels of the one or more selected Signature 1 and/or Signature 2 and/or Signature 3 and/or Signature 4 markers in steps d) and e); and g) identifying a difference between the first difference and the second difference, wherein the difference identified in g) is indicative of the efficacy of the treatment for the prostate cancer, or the progression or regression of the prostate cancer, or whether the compound is capable of ameliorating or treating the prostate cancer, respectively, in the subject.

In a third aspect, the methods provided in this invention for assessing the efficacy of a treatment for prostate cancer, monitoring the progression or regression of prostate cancer, or identifying a compound capable of ameliorating or treating prostate cancer, respectively, in a subject comprising: a) measuring the levels of one or more markers selected from the group consisting of Signature 1 and/or Signature 2 and/or Signature 3 and/or Signature 4 (Tables 1 and/or 2 and/or 3 and/or 4, respectively) in a population of the subject's macrophage cells before the treatment, or at a first time point, or before administration of the compound, respectively; b) identifying a first difference between the measured levels of the one or more selected Signature 1 and/or Signature 2 and/or Signature 3 and/or Signature 4 markers in step (a) and the levels of the one or more selected Signature 1 and/or Signature 2 and/or Signature 3 and/or Signature 4 markers in a control (e.g., a healthy control cell, or a control cell from a healthy subject) before the treatment, or at the first time point, or before administration of the compound, respectively; c) measuring the levels of the one or more selected Signature 1 and/or Signature 2 and/or Signature 3 and/or Signature 4 markers in a population of the subject's macrophage cells after the treatment, or at a second time point, or after administration of the compound, respectively; d) identifying a second difference between the measured levels of the one or more selected Signature 1 and/or Signature 2 and/or Signature 3 and/or Signature 4 markers in step c) and the levels of the one or more selected Signature 1 and/or Signature 2 and/or Signature 3 and/or Signature 4 markers in a control after the treatment, or at the second time point, or after administration of the compound, respectively; and e) identifying a difference between the first difference and the second difference, wherein the difference identified in e) is indicative of the efficacy of the treatment for the prostate cancer, or the progression or regression of the prostate cancer, or whether the compound is capable of ameliorating or treating the prostate cancer, respectively, in the subject.

In the second and third aspects, the selected markers comprise one or more (e.g., two, three, four, five, six, seven, eight, nine, ten, twenty, thirty, forty, fifty, one-hundred, one-hundred seventeen, or any increment between those values) of Signature 1, or one or more (e.g., two, three, four, five, six, seven, eight, nine, ten, eleven, twelve, thirteen, fourteen, fifteen, sixteen, seventeen, or eighteen) of Signature 2, or one or more (e.g., two, two, three, four, five, six, seven, eight, nine, ten, eleven, twelve, thirteen, fourteen, fifteen, sixteen, seventeen, or eighteen) markers of Signature 3, or one or more (e.g., two, two, three, four, five, six, seven, eight, nine, or ten) markers of Signature 4. In some embodiments, the selected markers are up-regulated (see Tables 1 and/or 2 and/or 3 and/or 4 for up-regulated markers) in prostate cancer patients. In some embodiments, the selected markers are down-regulated (see Table 1 for down-regulated markers) in prostate cancer patients. In some embodiments, the selected markers comprise at least one Signature 1 marker that is up-regulated and at least one Signature 1 marker that is down-regulated.

In some embodiments, two sub-populations of phagocytic cells are used in the methods of this invention, i.e., phagocytic cells that have a DNA content greater than 2n (the >2n phagocytic cells) and phagocytic cells that have a DNA content of 2n (the =2n phagocytic cells). In those embodiments, the levels of the selected markers in the >2n phagocytic cells are compared to the =2n phagocytic cells to identify one or more difference. The identified differences indicate whether the subject has prostate cancer, or has a risk of developing prostate cancer, or has a progressing or progressive prostate cancer.

In some embodiments, the levels of one or more markers from Tables 1 or 2 or 3 or 4 are measured in combination with measuring the levels of one or more markers from a different table from among Tables 1, 2, 3, and 4.

In various embodiments of the present invention, at least one or more of the selected markers (Signature 1 markers or Signature 2 markers or Signature 4 markers or Signature 4 markers) may be used in addition to a biological marker different from any of the selected markers. In some embodiments, such biological markers may be known markers for prostate cancer. In some embodiments, such biological markers and the substituted selected markers may belong to the same signaling or biological pathway (e.g., a protein synthesis pathway, Th1 cytokine production pathway, transcription pathway, programmed cell death pathway), or may have similar biological function or activity (e.g., protein synthesis, Th1 cytokine production, nucleotide binding, protein binding, transcription, a receptor for purines coupled to G-proteins, inhibition of programmed cell death, neutrophil activation, an IL-8 receptor, an HSP70-interacting protein, stimulating ATPase activity), or may be regulated by a common protein, or may belong to the same protein complex (e.g., an HSP70 protein complex).

In various embodiments of the present invention, a population of the subject's macrophage cells is used as the selected phagocytic cells for measuring the levels of the selected markers (e.g., Signature 1 and/or Signature 2 markers and/or Signature 3 markers and/or Signature 4 markers) and a population of the subject's T-cells is used as the selected non-phagocytic cells for measuring the levels of the selected markers (e.g., Signature 1 and/or Signature 2 markers and/or Signature 3 markers and/or Signature 4 markers).

The gene names/descriptions provided in Tables 1 and 2 and 3 and 4 are merely illustrative. The markers of this invention encompass all forms and variants of any specifically described markers, including, but not limited to, polymorphic or allelic variants, isoforms, mutants, derivatives, precursors including nucleic acids and pro-proteins, cleavage products, and structures comprised of any of the markers as constituent subunits of the fully assembled structure.

A "patient", "subject", or "individual" are used interchangeably and refer to either a human or a non-human animal. These terms include mammals, such as humans, primates, livestock animals (e.g., bovines, porcines), companion animals (e.g., canines, felines) and rodents (e.g., mice and rats).

As used herein, the terms "normal control", "healthy control", and "not-diseased cells" likewise mean a sample (e.g., cells, serum, tissue) taken from a source (e.g., subject, control subject, cell line) that does not have the condition or disease being assayed and therefore may be used to determine the baseline for the condition or disorder being measured. A control subject refers to any individual that has not been diagnosed as having the disease or condition being assayed. It is also understood that the control subject, normal control, and healthy control, include data obtained and used as a standard, i.e. it can be used over and over again for multiple different subjects. In other words, for example, when comparing a subject sample to a control sample, the data from the control sample could have been obtained in a different set of experiments, for example, it could be an average obtained from a number of healthy subjects and not actually obtained at the time the data for the subject was obtained.

The term "diagnosis" as used herein refers to methods by which the skilled artisan can estimate and/or determine whether or not a patient is suffering from a given disease or condition. In some embodiments, the term "diagnosis" also refers to staging (e.g., Stage I, II, III, or IV) of cancer. The skilled artisan often makes a diagnosis on the basis of one or more diagnostic indicators, e.g., a marker, the presence, absence, amount, or change in amount of which is indicative of the presence, severity, or absence of the condition.

The term "prognosis" as used herein refers to is used herein to refer to the likelihood of prostate cancer progression, including recurrence of prostate cancer, and/or evaluation of whether the prostate cancer is aggressive or indolent.

The disclosure of the International Applications PCT/US11/44969, PCT/US11/45018, and PCT/US09/31395 and U.S. Provisional Applications 61/660,518 and 61/660,427 are incorporated herein by reference for all purposes.

Each embodiment described herein may be combined with any other embodiment described herein.

Methods using the prostate cancer markers described herein provide high specificity, sensitivity, and accuracy in detecting and diagnosing prostate cancer. The methods also eliminate the "inequality of baseline" that is known to occur among individuals due to intrinsic (e.g., age, gender, ethnic background, health status and the like) and temporal variations in marker expression. Additionally, by using a comparison of phagocytes and non-phagocytes from the same individual, the methods also allow detection, diagnosis, and treatment to be personalized to the individual. Accordingly, in some embodiments, the invention provides non-invasive assays for the early detection of prostate cancer, i.e., before the prostate cancer can be diagnosed by conventional diagnostic techniques, e.g., imaging techniques, and, therefore, provide a foundation for improved decision-making relative to the needs and strategies for intervention, prevention, and treatment of individuals with such disease or condition.

The methods described herein are supported by whole genome microarray data of total RNA samples isolated from macrophages and from non-phagocytic T cells. The samples were obtained from human subjects with and without prostate cancer. The data from these microarray experiments demonstrate that macrophage-T cell comparisons easily and accurately differentiate between prostate cancer patients and human subjects without prostate cancer.

The methods of this invention can be used together with any known diagnostic methods, such as physical inspection, visual inspection, biopsy, scanning, histology, radiology, imaging, ultrasound, use of a commercial kit, genetic testing, immunological testing, analysis of bodily fluids, or monitoring neural activity.

Phagocytic cells that can be used in the methods of this invention include all types of cells that are capable of ingesting various types of substances (e.g., apoptotic cells, infectious agents, dead cells, viable cells, cell-free DNAs, cell-free RNAs, cell-free proteins). In some embodiments, the phagocytic cells are neutrophils, macrophages, monocytes, dendritic cells, foam cells, mast cells, eosinophils, or keratinocytes. In some embodiments, the phagocytic cells can be a mixture of different types of phagocytic cells. In some embodiments, the phagocytic cells can be activated phagocytic cells, e.g., activated macrophages or neutrophils. In some embodiments, a phagocyte is a histiocyte, e.g., a Langerhans cell.

As used herein, "treating" prostate cancer refers to taking steps to obtain beneficial or desired results, including clinical results. Beneficial or desired clinical results include, but are not limited to, alleviation or amelioration of one or more symptoms associated with diseases or conditions.

As used herein, "administering" or "administration of" a compound or an agent to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow, or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient. In some embodiments, a compound or an agent is administered orally, e.g., to a subject by ingestion, or intravenously, e.g., to a subject by injection. In some embodiments, the orally administered compound or agent is in an extended release or slow release formulation, or administered using a device for such slow or extended release.

In certain embodiments, markers used in the methods of invention are up-regulated or activated in phagocytes (e.g., macrophages or neutrophils) compared to non-phagocytes. In certain embodiments, markers used in the methods of invention are down-regulated or inhibited in phagocytes (e.g., macrophages or neutrophils) compared to non-phagocytes. As used herein, "up-regulation or up-regulated" can refer to an increase in expression levels (e.g., gene expression or protein expression), gene copy numbers, gene dosages, and other qualitative or quantitative detectable state of the markers. Similarly, "down-regulation or down-regulated" can refer to a decrease in expression levels, gene copy numbers, gene dosages, and other qualitative or quantitative detectable state of the markers. As used herein, "activation or activated" can refer to an active state of the marker, e.g., a phosphorylation state, a DNA methylation state, or a DNA acetylation state. Similarly, "inhibition or inhibited" can refer to a repressed state or an inactivated state of the marker, e.g., a de-phosphorylation state, a ubiquitination state, or a DNA de-methylation state.

In certain embodiments, methods of this invention also comprise at least one of the following steps before determination of various levels: i) lysing the phagocytic or non-phagocytic cells; and ii) extracting cellular contents from the lysed cells. Any known cell lysis and extraction methods can be used herein. In certain embodiments, at least one or more prostate cancer markers are present in the phagocytes. In certain embodiments, there is no marker present in the cellular contents of the non-phagocytic cells.

In certain embodiments, the phagocytic cells and/or non-phagocytic cells are isolated from a bodily fluid sample, tissues, or population of cells. Exemplary bodily fluid samples can be whole blood, urine, stool, saliva, lymph fluid, cerebrospinal fluid, synovial fluid, cystic fluid, ascites, pleural effusion, fluid obtained from a pregnant woman in the first trimester, fluid obtained from a pregnant woman in the second trimester, fluid obtained from a pregnant woman in the third trimester, maternal blood, amniotic fluid, chorionic villus sample, fluid from a preimplantation embryo, maternal urine, maternal saliva, placental sample, fetal blood, lavage and cervical vaginal fluid, interstitial fluid, buccal swab sample, sputum, bronchial lavage, Pap smear sample, or ocular fluid. In some embodiments, the phagocytic cells or non-phagocytic cells are isolated from white blood cells.

In the methods of this invention, cell separation/isolation/purification methods are used to isolate populations of cells from bodily fluid sample, cells, or tissues of a subject. A skilled worker can use any known cell separation/isolation/purification techniques to isolate phagocytic cells and non-phagocytic cells from a bodily fluid. Exemplary techniques include, but are not limited to, using antibodies, flow cytometry, fluorescence activated cell sorting, filtration, gradient-based centrifugation, elution, microfluidics, magnetic separation technique, fluorescent-magnetic separation technique, nanostructure, quantum dots, high throughput microscope-based platform, or a combination thereof.

In certain embodiments, the phagocytic cells and/or non-phagocytic cells are isolated by using a product secreted by the cells. In certain embodiments, the phagocytic cells and/or non-phagocytic cells are isolated by using a cell surface target (e.g., receptor protein) on the surface of the cells. In some embodiments, the cell surface target is a protein that has been engulfed by phagocytic cells. In some embodiments, the cell surface target is expressed by cells on their plasma membranes. In some embodiments, the cell surface target is an exogenous protein that is translocated on the plasma membranes, but not expressed by the cells (e.g., the phagocytic cells). In some embodiments, the cell surface target is a marker of prostate cancer.

In certain aspects of the methods described herein, analytes include nucleic acids, proteins, or any combinations thereof. In certain aspects of the methods described herein, markers include nucleic acids, proteins, or any combinations thereof. As used herein, the term "nucleic acid" is intended to include DNA molecules (e.g., cDNA or genomic DNA), RNA molecules (e.g., mRNA), DNA-RNA hybrids, and analogs of the DNA or RNA generated using nucleotide analogs. The nucleic acid molecule can be a nucleotide, oligonucleotide, double-stranded DNA, single-stranded DNA, multi-stranded DNA, complementary DNA, genomic DNA, non-coding DNA, messenger RNA (mRNAs), micro-RNA (miRNAs), small nucleolar RNA (snoRNAs), ribosomal RNA (rRNA), transfer RNA (tRNA), small interfering RNA (siRNA), heterogeneous nuclear RNAs (hnRNA), or small hairpin RNA (shRNA). In some embodiments, the nucleic acid is a transrenal nucleic acid. A transrenal nucleic acid is an extracellular nucleic acid that is excreted in the urine. See, e.g., U.S. Patent Publication No. 20100068711 and U.S. Patent Publication No. 20120021404.

As used herein, the term "amino acid" includes organic compounds containing both a basic amino group and an acidic carboxyl group. Included within this term are natural amino acids (e.g., L-amino acids), modified and unusual amino acids (e.g., D-amino acids and β-amino acids), as well as amino acids which are known to occur biologically in free or combined form but usually do not occur in proteins. Natural protein occurring amino acids include alanine, arginine, asparagine, aspartic acid, cysteine, glutamic acid, glutamine, glycine, histidine, isoleucine, leucine, lysine, methionine, phenylalanine, serine, threonine, tyrosine, tryptophan, proline, and valine. Natural non-protein amino acids include arginosuccinic acid, citrulline, cysteine sulfuric acid, 3,4-dihydroxyphenylalanine, homocysteine, homoserine, ornithine, 3-monoiodotyrosine, 3,5-diiodotryosine, 3, 5, 5-triiodothyronine, and 3,3',5,5'-tetraiodothyronine. Modified or unusual amino acids include D-amino acids, hydroxylysine, 4-hydroxyproline, N-Cbz-protected amino acids, 2,4-diaminobutyric acid, homoarginine, norleucine, N-methylaminobutyric acid, naphthylalanine, phenylglycine, α-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

As used herein, the term "peptide" includes compounds that consist of two or more amino acids that are linked by means of a peptide bond. Peptides may have a molecular weight of less than 10,000 Daltons, less than 5,000 Daltons, or less than 2,500 Daltons. The term "peptide" also includes compounds containing both peptide and non-peptide components, such as pseudopeptide or peptidomimetic residues or other non-amino acid components. Such compounds containing both peptide and non-peptide components may also be referred to as a "peptide analog."

As used herein, the term "protein" includes compounds that consist of amino acids arranged in a linear chain and joined together by peptide bonds between the carboxyl and amino groups of adjacent amino acid residues. Proteins used in methods of the invention include, but are not limited to, amino acids, peptides, antibodies, antibody fragments, cytokines, lipoproteins, or glycoproteins.

As used herein, the term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules, and antibody fragments (e.g., Fab or F(ab')$_2$, and Fv). For the structure and properties of the different classes of antibodies, see e.g., Basic and Clinical Immunology, 8th Edition, Daniel P. Sties, Abba I. Ten and Tristram G. Parsolw (eds), Appleton & Lange, Norwalk, Conn., 1994, page 71 and Chapter 6.

As used herein, the term "cytokine" refers to a secreted protein or active fragment or mutant thereof that modulates the activity of cells of the immune system. Examples of cytokines include, without limitation, interleukins, interferons, chemokines, tumor necrosis factors, colony-stimulating factors for immune cell precursors, and the like.

As used herein, the term "lipoprotein" includes negatively charged compositions that comprise a core of hydrophobic cholesteryl esters and triglyceride surrounded by a surface layer of amphipathic phospholipids with which free cholesterol and apolipoproteins are associated. Lipoproteins may be characterized by their density (e.g. very-low-density lipoprotein (VLDL), low-density lipoprotein (LDL) and high density lipoprotein (HDL)), which is determined by their size, the relative amounts of lipid and protein. Lipoproteins may also be characterized by the presence or absence of particular modifications (e.g. oxidization, acetylation, or glycation).

As used herein, the term "glycoprotein" includes glycosides which have one or more oligo- or polysaccharides covalently attached to a peptide or protein. Exemplary glycoproteins can include, without limitation, immunoglobulins, members of the major histocompatibility complex, collagens, mucins, glycoprotein IIb/IIIa, glycoprotein-41 (gp41) and glycoprotein-120 (gp12), follicle-stimulating hormone, alpha-fetoprotein, erythropoietin, transferrins, alkaline phosphatase, and lectins.

In some embodiments of the invention, a sample may comprise one or more stabilizers for a cell or an analyte such as DNA, RNA, and/or protein. For example, a sample may comprise a DNA stabilizer, an RNA stabilizer, and/or a protein stabilizer. Stabilizers are well known in the art and include, for example, DNAse inhibitors, RNAse inhibitors, and protease inhibitors or equivalents thereof.

In some embodiments of the invention, levels of at least one or more prostate cancer markers are compared. This comparison can be quantitative or qualitative. Quantitative measurements can be taken using any of the assays described herein. For example, sequencing, direct sequencing, random shotgun sequencing, Sanger dideoxy termination sequencing, targeted sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), polymerase chain reaction (PCR) analysis, quantitative PCR, real-time PCR, fluorescence assay, colorimetric assay, chemiluminescent assay, or a combination thereof.

Quantitative comparisons can include statistical analyses such as t-test, ANOVA, Krustal-Wallis, Wilcoxon, Mann-Whitney, and odds ratio. Quantitative differences can include differences in the levels of markers between levels or differences in the numbers of markers present between levels, and combinations thereof. Examples of levels of the markers can be, without limitation, gene expression levels, nucleic acid levels, and protein levels. Qualitative differences can include, but are not limited to, activation and inactivation, protein degradation, nucleic acid degradation, and covalent modifications.

In certain embodiments of the invention, the level is a nucleic acid level or a protein level, or a combination thereof. The level can be qualitatively or quantitatively determined.

A nucleic acid level can be, without limitation, a genotypic level, a single nucleotide polymorphism level, a gene mutation level, a gene copy number level, a DNA methylation level, a DNA acetylation level, a chromosome dosage level, a gene expression level, or a combination thereof.

The nucleic acid level can be determined by any methods known in the art to detect genotypes, single nucleotide polymorphisms, gene mutations, gene copy numbers, DNA methylation states, DNA acetylation states, chromosome dosages. Exemplary methods include, but are not limited to, polymerase chain reaction (PCR) analysis, sequencing analysis, electrophoretic analysis, restriction fragment length polymorphism (RFLP) analysis, Northern blot analysis, quantitative PCR, reverse-transcriptase-PCR analysis (RT-PCR), allele-specific oligonucleotide hybridization analysis, comparative genomic hybridization, heteroduplex mobility assay (HMA), single strand conformational polymorphism (SSCP), denaturing gradient gel electrophisis (DGGE), RNAase mismatch analysis, mass spectrometry, tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), surface plasmon resonance, Southern blot analysis, in situ hybridization, fluorescence in situ hybridization (FISH), chromogenic in situ hybridization (CISH), immunohistochemistry (IHC), microarray, comparative genomic hybridization, karyotyping, multiplex ligation-dependent probe amplification (MLPA), Quantitative Multiplex PCR of Short Fluorescent Fragments (QMPSF), microscopy, methylation specific PCR (MSP) assay, HpaII tiny fragment Enrichment by Ligation-mediated PCR (HELP) assay, radioactive acetate labeling assays, colorimetric DNA acetylation assay, chromatin immunoprecipitation combined with microarray (ChIP-on-chip) assay, restriction landmark genomic scanning, Methylated DNA immunoprecipitation (MeDIP), molecular break light assay for DNA adenine methyltransferase activity, chromatographic separation, methylation-sensitive restriction enzyme analysis, bisulfite-driven conversion of non-methylated cytosine to uracil, co-amplification at lower denaturation temperature-PCR (COLD-PCR), multiplex PCR, methyl-binding PCR analysis, or a combination thereof.

As used herein, the term "sequencing" is used in a broad sense and refers to any technique known in the art that allows the order of at least some consecutive nucleotides in at least part of a nucleic acid to be identified, including without limitation at least part of an extension product or a vector insert. Exemplary sequencing techniques include targeted sequencing, single molecule real-time sequencing, whole transcriptome shotgun sequencing ("RNA-seq"), electron microscopy-based sequencing, transistor-mediated sequencing, direct sequencing, random shotgun sequencing, Sanger dideoxy termination sequencing, exon sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD® sequencing, MS-PET sequencing, mass spectrometry, and a combination thereof. In some embodiments, sequencing comprises an detecting the sequencing product using an instrument, for example but not limited to an ABI PRISM® 377 DNA Sequencer, an ABI PRISM® 310, 3100, 3100-Avant, 3730, or 373OxI Genetic Analyzer, an ABI PRISM® 3700 DNA Analyzer, or an Applied Biosystems SOLiD™ System (all from Applied Biosystems), a Genome Sequencer 20 System (Roche Applied Science), or a mass spectrometer. In certain embodiments, sequencing comprises emulsion PCR. In certain embodiments, sequencing comprises a high throughput sequencing technique, for example but not limited to, massively parallel signature sequencing (MPSS).

In further embodiments of the invention, a protein level can be a protein expression level, a protein activation level, or a combination thereof. In some embodiments, a protein activation level can comprise determining a phosphorylation state, an ubiquitination state, a myristoylation state, or a conformational state of the protein.

A protein level can be detected by any methods known in the art for detecting protein expression levels, protein phosphorylation state, protein ubiquitination state, protein myristoylation state, or protein conformational state. In some embodiments, a protein level can be determined by an immunohistochemistry assay, an enzyme-linked immunosorbent assay (ELISA), in situ hybridization, chromatography, liquid chromatography, size exclusion chromatography, high performance liquid chromatography (HPLC), gas chromatography, mass spectrometry, tandem mass spectrometry, matrix assisted laser desorption/ionization-time of flight (MALDI-TOF) mass spectrometry, electrospray ionization (ESI) mass spectrometry, surface-enhanced laser deorption/ionization-time of flight (SELDI-TOF) mass spectrometry, quadrupole-time of flight (Q-TOF) mass spectrometry, atmospheric pressure photoionization mass spectrometry (APPI-MS), Fourier transform mass spectrometry (FTMS), matrix-assisted laser desorption/ionization-Fourier transform-ion cyclotron resonance (MALDI-FT-ICR) mass spectrometry, secondary ion mass spectrometry (SIMS), radioimmunoassays, microscopy, microfluidic chip-based assays, surface plasmon resonance, sequencing, Western blotting assay, or a combination thereof.

As used herein, the "difference" between different levels detected by the methods of this invention can refer to different gene copy numbers, different DNA, RNA, or protein expression levels, different DNA methylation states, different DNA acetylation states, and different protein modification states. The difference can be a difference greater than 1 fold. In some embodiments, the difference is a 1.05-fold, 1.1-fold, 1.2-fold, 1.3-fold, 1.4-fold, 1.5-fold, 2-fold, 2.5-fold, 3-fold, 4-fold, 5-fold, 6-fold, 7-fold, 8-fold, 9-fold, or 10-fold difference. In some embodiments, the difference is any fold difference between 1-10, 2-10, 5-10, 10-20, or 10-100 fold.

In some embodiments, the difference is differential gene expression (DGE), e.g. DGE of phagocytes vs. non-phagocytes. DGE can be measured as $X=\log_2(Y_P)-\log_2(Y_{NP})$. The DGE may be any number, provided that it is significantly different between the phagocytes and the non-phagocytes. For example, a 2-fold increased in gene expression could be represented as $X=\log_2(Y_P)-\log_2(Y_{NP})=\log_2(Y_P/Y_{NP})=\log_2(2)=1$, while a 2-fold decrease in gene expression could be represented as $X=\log_2(Y_P)-\log_2(Y_{NP})=\log_2(Y_P/Y_{NP})=\log_2(½)=-1$. Down-regulated genes have $X<0$, while up-regulated genes have $X>0$. See, e.g., Efron, J Am Stat Assoc 104:1015-1028 (2009).

A general principle of assays to detect markers involves preparing a sample or reaction mixture that may contain the marker (e.g., one or more of DNA, RNA, or protein) and a probe under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In certain exemplary embodiments, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, U.S. Pat. Nos. 5,631,169 and 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. A FRET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C, 1991, Anal. Chem. 63:2338 2345 and Szabo et al, 1995, Curr. Opin. Struct. Biol. 5:699 705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes may be separated from uncomplexed assay components through a series of centrifugal steps, due to the different sedimentation equilibria of complexes based on their different sizes and densities (see, for example, Rivas and Minton (1993) Trends Biochem. Sci. 18:284). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the marker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard (1998) J. Mol. Recognit. 11:141; Hage and Tweed (1997) J. Chromatogr. B. Biomed. Sci. Appl. 12:499). Gel electrophoresis may also be employed to separate complexed assay components from unbound components (see, e.g., Ausubel et al, ed., Current Protocols in Molecular Biology, John Wiley & Sons, New York, 1987 1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In certain exemplary embodiments, the level of mRNA corresponding to the marker can be determined either by in situ and/or by in vitro formats in a biological sample using methods known in the art. Many expression detection methods use isolated RNA. For in vitro methods, any RNA isolation technique that does not select against the isolation of mRNA can be utilized for the purification of RNA from blood cells (see, e.g., Ausubel et al, ed., Current Protocols in Molecular Biology, John Wiley & Sons, New York 1987 1999). Additionally, large numbers of cells and/or samples can readily be processed using techniques well known to those of skill in the art, such as, for example, the single-step RNA isolation process of Chomczynski (1989, U.S. Pat. No. 4,843,155).

Isolated mRNA can be used in hybridization or amplification assays that include, but are not limited to, Southern or Northern analyses, polymerase chain reaction analyses and probe arrays. In certain exemplary embodiments, a diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to an mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in a gene chip array. A skilled artisan can readily adapt known mRNA detection methods for use in detecting the level of mRNA encoded by the markers of the present invention.

An alternative method for determining the level of mRNA corresponding to a marker of the present invention in a sample involves the process of nucleic acid amplification, e.g., by RT-PCR (the experimental embodiment set forth in U.S. Pat. Nos. 4,683,195 and 4,683,202), COLD-PCR (Li et al. (2008) Nat. Med. 14:579), ligase chain reaction (Barany, 1991, Proc. Natl. Acad. Sci. USA, 88:189), self sustained sequence replication (Guatelli et al., 1990, Proc. Natl. Acad. Sci. USA 87:1874), transcriptional amplification system (Kwoh et al. (1989) Proc. Natl. Acad. Sci. USA 86:1173), Q-Beta Replicase (Lizardi et al. (1988) Bio/Technology 6:1197), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the sample (e.g., a bodily fluid (e.g., blood cells)) prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations may be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in a patient sample from one source to a patient sample from another source, e.g., to compare a population of phagocytic from an individual to a population of non-phagocytic cells from the individual.

In one embodiment of this invention, a protein or polypeptide corresponding to a marker is detected. In certain embodiments, an agent for detecting a protein or polypeptide can be an antibody capable of binding to the polypeptide, such as an antibody with a detectable label. As used herein, the term "labeled," with regard to a probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. Antibodies can be polyclonal or monoclonal. An intact antibody, or a fragment thereof (e.g., Fab or F(ab')2) can be used. In one format, antibodies, or antibody fragments, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well known supports or carriers include glass, polystyrene, polypropylene, polyethylene, dextran, nylon, amylases, natural and modified celluloses, polyacrylamides, gabbros, magnetite and the like.

A variety of formats can be employed to determine whether a sample contains a protein that binds to a given antibody. Examples of such formats include, but are not limited to, competitive and non-competitive immunoassay, enzyme immunoassay (EIA), radioimmunoassay (RIA), antigen capture assays, two-antibody sandwich assays, Western blot analysis, enzyme linked immunoabsorbant assay (ELISA), a planar array, a colorimetric assay, a chemiluminescent assay, a fluorescent assay, and the like. Immunoassays, including radioimmmunoassays and enzyme-linked immunoassays, are useful in the methods of the present invention. A skilled artisan can readily adapt known protein/antibody detection methods for use in determining whether cells (e.g., bodily fluid cells such as blood cells) express a marker of the present invention.

One skilled in the art will know many other suitable carriers for binding antibody or antigen, and will be able to adapt such support for use with the present invention. For example, protein isolated from cells (e.g., bodily fluid cells such as blood cells) can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

In certain exemplary embodiments, assays are provided for diagnosis, prognosis, assessing the risk of developing prostate cancer, assessing the efficacy of a treatment, monitoring the progression or regression of prostate cancer, and identifying a compound capable of ameliorating or treating prostate cancer. An exemplary method for these methods involves obtaining a bodily fluid sample from a test subject, isolating phagocytes and non-phagocytes, and contacting the phagocytes and non-phagocytes with a compound or an agent capable of detecting one or more of the markers of the disease or condition, e.g., marker nucleic acid (e.g., mRNA, genomic DNA), marker peptide (e.g., polypeptide or protein), marker lipid (e.g., cholesterol), or marker metabolite (e.g., creatinine) such that the presence of the marker is detected. In one embodiment, an agent for detecting marker mRNA or genomic DNA is a labeled nucleic acid probe capable of hybridizing to marker mRNA or genomic DNA. The nucleic acid probe can be, for example, a full-length marker nucleic acid or a portion thereof. Other suitable probes for use in the diagnostic assays of the invention are described herein.

As used herein, a compound capable of ameliorating or treating prostate cancer can include, without limitations, any substance that can improve symptoms or prognosis, prevent progression of the prostate cancer, promote regression of the prostate cancer, or eliminate the prostate cancer.

The methods of the invention can also be used to detect genetic alterations in a marker gene, thereby determining if a subject with the altered gene is at risk for developing prostate cancer characterized by misregulation in a marker protein activity or nucleic acid expression. In certain embodiments, the methods include detecting, in phagocytes, the presence or absence of a genetic alteration characterized by an alteration affecting the integrity of a gene encoding a marker peptide and/or a marker gene. For example, such genetic alterations can be detected by ascertaining the existence of at least one of: 1) a deletion of one or more nucleotides from one or more marker genes; 2) an addition of one or more nucleotides to one or more marker genes; 3) a substitution of one or more nucleotides of one or more marker genes, 4) a chromosomal rearrangement of one or more marker genes; 5) an alteration in the level of a messenger RNA transcript of one or more marker genes; 6) aberrant modification of one or more marker genes, such as of the methylation pattern of the genomic DNA; 7) the presence of a non-wild type splicing pattern of a messenger RNA transcript of one or more marker genes; 8) a non-wild type level of a one or more marker proteins; 9) allelic loss of one or more marker genes; and 10) inappropriate post-translational modification of one or more marker proteins. As described herein, there are a large number of assays known in the art which can be used for detecting alterations in one or more marker genes.

In certain embodiments, detection of the alteration involves the use of a probe/primer in a polymerase chain reaction (PCR) (see, e.g., U.S. Pat. Nos. 4,683,195, 4,683,202 and 5,854,033), such as real-time PCR, COLD-PCR (Li et al. (2008) Nat. Med. 14:579), anchor PCR, recursive PCR or RACE PCR, or, alternatively, in a ligation chain reaction (LCR) (see, e.g., Landegran et al. (1988) Science 241:1077; Prodromou and Pearl (1992) Protein Eng. 5:827; and Nakazawa et al. (1994) Proc. Natl. Acad. Sci. USA 91:360), the latter of which can be particularly useful for detecting point mutations in a marker gene (see Abravaya et al. (1995) Nucleic Acids Res. 23:675). This method can include the steps of collecting a sample of cell free bodily fluid from a subject, isolating nucleic acid (e.g., genomic, mRNA or both) from the sample, contacting the nucleic acid sample with one or more primers which specifically hybridize to a marker gene under conditions such that hybridization and amplification of the marker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al., (1990) Proc. Natl. Acad. Sci. USA 87:1874), transcriptional amplification system (Kwoh et al., (1989) Proc. Natl. Acad. Sci. USA 86:1173), Q Beta Replicase (Lizardi et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in one or more marker genes from a sample can be identified by alterations in restriction enzyme cleavage patterns. For example, sample and control DNA is isolated, optionally amplified, digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in one or more of the markers described herein can be identified by hybridizing a sample and control nucleic acids, e.g., DNA or RNA, to high density arrays containing hundreds or thousands of oligonucleotides probes (Cronin et al. (1996) Human Mutation 7: 244; Kozal et al. (1996) Nature Medicine 2:753). For example, genetic mutations in a marker nucleic acid can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence a marker gene and detect mutations by comparing the sequence of the sample marker gene with the corresponding wild-type (control) sequence. Examples of sequencing reactions include those based on techniques developed by Maxam and Gilbert ((1977) Proc. Natl. Acad. Sci. USA 74:560) or Sanger ((1977) Proc. Natl. Acad. Sci. USA 74:5463). It is also contemplated that any of a variety of automated sequencing procedures can be utilized when performing the diagnostic assays ((1995) Biotechniques 19:448), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147).

Other methods for detecting mutations in a marker gene include methods in which protection from cleavage agents is used to detect mismatched bases in RNA/RNA or RNA/DNA heteroduplexes (Myers et al. (1985) Science 230: 1242). In general, the art technique of "mismatch cleavage" starts by providing heteroduplexes formed by hybridizing (labeled) RNA or DNA containing the wild-type marker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with 51 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397; Saleeba et al. (1992) Methods Enzymol. 217:286. In one embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in marker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) Carcinogenesis 15:1657). According to an exemplary embodiment, a probe based on a marker sequence, e.g., a wild-type marker sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in marker genes. For example, single strand conformation polymorphism (SSCP) may be used to detect differences in electrophoretic mobility between mutant and wild type nucleic acids (Orita et al. (1989) Proc. Natl. Acad. Sci. USA 86:2766, see also Cotton (1993) Mutat. Res. 285:125; and Hayashi (1992) Genet. Anal. Tech. Appl. 9:73). Single-stranded DNA fragments of sample and control marker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucl. Acids Res. 17:2437) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci. USA 88:189). In such cases, ligation will occur only if there is a perfect match at the 3' end of the 5' sequence making it possible to detect the presence of a known mutation at a specific site by looking for the presence or absence of amplification.

An exemplary method for detecting the presence or absence of an analyte (e.g., DNA, RNA, protein, polypeptide, or the like) corresponding to a marker of the invention in a biological sample involves obtaining a bodily fluid sample (e.g., blood) from a test subject and contacting the bodily fluid sample with a compound or an agent capable of detecting one or more markers. Detection methods described herein can be used to detect one or more markers in a biological sample in vitro as well as in vivo. For example, in vitro techniques for detection of mRNA include Northern hybridizations and in situ hybridizations. In vitro techniques for detection of a polypeptide corresponding to a marker of the invention include enzyme linked immunosorbent assays (ELISAs), Western blots, immunoprecipitations and immunofluorescence. In vitro techniques for detection of genomic DNA include Southern hybridizations. Furthermore, in vivo techniques for detection of a polypeptide corresponding to a marker of the invention include introducing into a subject a labeled antibody directed against the polypeptide. For example, the antibody can be labeled with a radioactive marker whose presence and location in a subject can be detected by standard imaging techniques. Because each marker is also an analyte, any method described herein to detect the presence or absence of a marker can also be used to detect the presence or absence of an analyte.

The markers useful in the methods of the invention can include any mutation in any one of the markers. Mutation sites and sequences can be identified, for example, by databases or repositories of such information, e.g., The Human Gene Mutation Database (www.hgmd.cf.ac.uk), the Single Nucleotide Polymorphism Database (dbSNP, www.ncbi.nlm.nih.gov/projects/SNP), and the Online Mendelian Inheritance in Man (OMIM) website (www.ncbi.nlm.nih.gov/omim).

The present invention also provides kits that comprise marker detection agents that detect at least one or more of the prostate cancer markers described herein.

The present invention also provides methods of treating or preventing prostate cancer in a subject comprising administering to said subject an agent that modulates the activity or expression or disrupts the function of at least one or more of the markers of this invention.

The one or more markers identified by this invention (e.g., markers in Tables 1 and 2 and 3 and 4) may be used in the treatment of prostate cancer. For example, a marker (e.g., a protein or gene) identified by the present invention may be used as a molecular target for a therapeutic agent. A marker identified by the invention also may be used in any of the other methods of the invention, e.g., for monitoring the progression or regression of a disease or condition. In certain embodiments, the one or more markers identified by the methods of this invention may have therapeutic potential. For example, if a marker is identified as being up-regulated (or down-regulated), see, for example, the up-regulated (or down-regulated) markers in Tables 1 and 2 and 3 and 4, or activated (or inhibited) in phagocytic cells from a subject having prostate cancer, a compound or an agent that is capable of down-regulating (or up-regulating) or inhibiting (or activating) said marker may be useful in treating prostate cancer. Similarly, a gene protein expression level, a protein expression level, or a combination thereof may be useful in this aspect of the invention.

Unless otherwise defined herein, scientific and technical terms used in this application shall have the meanings that are commonly understood by those of ordinary skill in the art. Generally, nomenclature used in connection with, and techniques of, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

All of the above, and any other publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention.

The following examples are set forth as being representative of the present invention. These examples are not to be construed as limiting the scope of the invention as these and other equivalent embodiments will be apparent in view of the present disclosure and accompanying claims.

EXAMPLES

Example 1: Identification of Signature 1

A microarray was used to search for a signature of normal vs. aggressive cancer in subtraction-normalized expression data collected from blood samples processed 4 hours after collection (FIG. 1). Based on this assay, the 117 genes of Signature 1 were selected and cross validated as described in Example 5, below. Signature 1 had a sensitivity (probability of correctly detecting aggressive cancer) of 61%, and a specificity (probability of correctly identifying normal patients) of 58%.

TABLE 1

Signature 1

| Signature 1 marker # | Illumina Transcript ID | Gene name | Aggressive cancer mean | Normal mean | Upregulated (UR) or downregulated (DR) in aggressive cancer |
|---|---|---|---|---|---|
| 1 | 15689 | OAS3 | −9.0142958 | −8.6439767 | Cancer DR |
| 2 | 14409 | RPL13L | −1.2329318 | −1.0853327 | Cancer DR |
| 3 | 20119 | RDH5 | 29.3184458 | 29.7644395 | Cancer DR |
| 4 | 18791 | SOX6 | −1.9161712 | −1.7990754 | Cancer DR |
| 5 | 10951 | OSBPL1A | −35.893494 | −48.758773 | Cancer UR |
| 6 | 28512 | GP5 | 10.9758038 | 3.5258523 | Cancer UR |
| 7 | 10695 | GPR89A | 10.5690901 | 10.9658205 | Cancer DR |
| 8 | 86688 | HS.336511 | −3.1086968 | −2.8816541 | Cancer DR |
| 9 | 10875 | TMEM80 | −47.885292 | −46.725592 | Cancer DR |
| 10 | 13640 | PPPDE2 | −160.41714 | −159.55055 | Cancer DR |
| 11 | 22832 | RYR3 | −1.3796285 | −1.265545 | Cancer DR |
| 12 | 168345 | RHBDD2 | 77.0791083 | 79.0695935 | Cancer DR |
| 13 | 25536 | MC1R | 74.1685045 | 74.8626128 | Cancer DR |
| 14 | 15079 | CCDC128 | 7.1783549 | −54.138047 | Cancer UR |
| 15 | 33909 | LOC285588 | 3.2824067 | −1.8452802 | Cancer UR |
| 16 | 7272 | ERGIC1 | −76.02445 | −74.709689 | Cancer DR |
| 17 | 177008 | H2BFWT | −1.1260872 | −0.9863237 | Cancer DR |
| 18 | 20474 | CYB561 | 124.258067 | 125.519911 | Cancer DR |
| 19 | 41366 | LOC643879 | −0.1453645 | 0.0472667 | Cancer DR |
| 20 | 18811 | RPL37 | 5.53447215 | 5.72682674 | Cancer DR |
| 21 | 180795 | UGT3A2 | 4.67348819 | −1.6783285 | Cancer UR |
| 22 | 2007 | TP53I3 | −141.98502 | −140.64734 | Cancer DR |
| 23 | 16880 | VWA5A | −19.190299 | −18.947648 | Cancer DR |
| 24 | 123241 | HS.571060 | −1.460709 | −1.3092629 | Cancer DR |
| 25 | 4653 | CREB1 | 1888.87492 | 1929.09126 | Cancer DR |
| 26 | 18195 | CYP4F2 | −2.3318799 | −2.2203552 | Cancer DR |
| 27 | 16552 | TNFRSF11A | −1.1759614 | −1.0106681 | Cancer DR |
| 28 | 5994 | OAS2 | −24.115038 | −23.431537 | Cancer DR |
| 29 | 75591 | HS.119922 | −0.9591632 | −0.8249897 | Cancer DR |
| 30 | 166060 | FLJ39632 | −0.3382191 | −0.1727163 | Cancer DR |

TABLE 1-continued

Signature 1

| Signature 1 marker # | Illumina Transcript ID | Gene name | Aggressive cancer mean | Normal mean | Upregulated (UR) or downregulated (DR) in aggressive cancer |
|---|---|---|---|---|---|
| 31 | 8229 | RP11-49G10.8 | −6.0144268 | −5.8367272 | Cancer DR |
| 32 | 18712 | KATNAL1 | 4.70953157 | −1.8584848 | Cancer UR |
| 33 | 30114 | GCNT2 | −0.1594717 | 0.0188688 | Cancer DR |
| 34 | 346904 | LOC729212 | −0.476 | −0.3228795 | Cancer DR |
| 35 | 163101 | IRF9 | −392.03757 | −380.96229 | Cancer DR |
| 36 | 33349 | LOC653216 | −1.0175463 | −0.8626032 | Cancer DR |
| 37 | 42341 | LOC440386 | −0.8536411 | −0.6714295 | Cancer DR |
| 38 | 6769 | INF2 | 3.25469335 | 3.48877586 | Cancer DR |
| 39 | 15843 | JARID2 | −380.58538 | −378.03988 | Cancer DR |
| 40 | 17229 | HNRNPM | 32.3962097 | 36.4189036 | Cancer DR |
| 41 | 1894 | IL5RA | 0.83011712 | 1.23681659 | Cancer DR |
| 42 | 182198 | YOD1 | −1.0684564 | −0.968089 | Cancer DR |
| 43 | 21388 | VHL | −153.61908 | −149.34478 | Cancer DR |
| 44 | 11812 | TRIM56 | 96.3762478 | 97.9483118 | Cancer DR |
| 45 | 347804 | LOC100130276 | 29.0218497 | 29.6648654 | Cancer DR |
| 46 | 27308 | UBE2I | −1.5908237 | −1.459543 | Cancer DR |
| 47 | 11362 | C8ORF30A | −2.8852459 | −2.7452391 | Cancer DR |
| 48 | 15490 | METT11D1 | 119.293311 | 120.326483 | Cancer DR |
| 49 | 29227 | ZSCAN22 | 0.547568 | 0.68218938 | Cancer DR |
| 50 | 16766 | ZNF385B | −0.7907855 | −0.6223701 | Cancer DR |
| 51 | 24801 | C20ORF94 | 0.40482839 | 0.81268385 | Cancer DR |
| 52 | 173747 | D4S234E | 531.294243 | 538.45889 | Cancer DR |
| 53 | 23467 | C7ORF20 | −33.821791 | −33.360883 | Cancer DR |
| 54 | 170201 | CCDC88C | 200.919891 | 203.185051 | Cancer DR |
| 55 | 2163 | KRT38 | 4.69638401 | −1.994684 | Cancer UR |
| 56 | 162122 | LOC727735 | 3.0613806 | −2.517745 | Cancer UR |
| 57 | 171831 | LOC732215 | −0.9351387 | −0.8075807 | Cancer DR |
| 58 | 343768 | LOC646353 | −0.8575194 | −0.7297925 | Cancer DR |
| 59 | 21343 | DPRX | 2.98927307 | −2.5628675 | Cancer UR |
| 60 | 23908 | SLC2A14 | −4.387825 | −4.1721651 | Cancer DR |
| 61 | 341890 | LOC732446 | −0.6644245 | −0.5321704 | Cancer DR |
| 62 | 33455 | RNF5P1 | −82.512422 | −80.617845 | Cancer DR |
| 63 | 22073 | MEST | −0.6877526 | −0.5880494 | Cancer DR |
| 64 | 338462 | LOC100130829 | 2.19340981 | −3.3179853 | Cancer UR |
| 65 | 31584 | LOC646223 | −4.695691 | −4.5120316 | Cancer DR |
| 66 | 13066 | C19ORF50 | −130.26601 | −128.0409 | Cancer DR |
| 67 | 11344 | VPS16 | −74.322484 | −71.72812 | Cancer DR |
| 68 | 28868 | TCEAL1 | −2.2433124 | −2.1065912 | Cancer DR |
| 69 | 6866 | TRIM28 | 43.6841007 | 44.7414677 | Cancer DR |
| 70 | 138370 | ANKRD13D | −54.17119 | −52.791341 | Cancer DR |
| 71 | 180926 | STX6 | −190.67106 | −189.13492 | Cancer DR |
| 72 | 28557 | AGFG2 | 45.1171985 | 45.500398 | Cancer DR |
| 73 | 179882 | IL17RD | 251.863927 | 258.077015 | Cancer DR |
| 74 | 162687 | BCR | 8.03158781 | 8.21889719 | Cancer DR |
| 75 | 176690 | SP100 | −15.413932 | −14.913489 | Cancer DR |
| 76 | 12053 | RASL10B | 3.75650279 | −2.8100791 | Cancer UR |
| 77 | 71322 | HS.13291 | −22.921159 | −22.296491 | Cancer DR |
| 78 | 17081 | C1ORF188 | 16.3121173 | 16.6240139 | Cancer DR |
| 79 | 13590 | NMNAT2 | 2.45548587 | −2.5067911 | Cancer UR |
| 80 | 7282 | CTHRC1 | 0.73487218 | 0.89298341 | Cancer DR |
| 81 | 18789 | ASS1 | −1.6801724 | −1.5631152 | Cancer DR |
| 82 | 352616 | LOC791120 | 163.351813 | 164.477126 | Cancer DR |
| 83 | 34136 | LOC649493 | −0.6295056 | −0.4795787 | Cancer DR |
| 84 | 346345 | FLJ31306 | 21.087961 | 21.6361882 | Cancer DR |
| 85 | 29344 | VGLL4 | 49.4631916 | 50.6916039 | Cancer DR |
| 86 | 336512 | LOC100132568 | −1.6082874 | −1.4598448 | Cancer DR |
| 87 | 6870 | TCEB3C | −1.8559032 | −1.7141848 | Cancer DR |
| 88 | 12233 | SBDSP | 29.0236367 | 29.6106915 | Cancer DR |
| 89 | 338504 | LOC100132535 | −0.0770285 | 0.17556409 | Cancer DR |
| 90 | 11118 | C8ORF37 | 609.519491 | 637.907911 | Cancer DR |
| 91 | 14405 | GOLGA8B | 2542.72843 | 2556.47364 | Cancer DR |
| 92 | 593 | SOLH | −5.8111916 | −5.2700925 | Cancer DR |
| 93 | 15604 | LOC400464 | 50.0233917 | 50.473654 | Cancer DR |
| 94 | 22944 | NKX6-1 | 2.1845754 | −2.4379099 | Cancer UR |
| 95 | 163801 | LOC442517 | −0.1049745 | 0.0275036 | Cancer DR |
| 96 | 29810 | ATP1B4 | 2.37077671 | −2.1346992 | Cancer UR |
| 97 | 167794 | USP41 | −2.2619871 | −2.0813413 | Cancer DR |
| 98 | 388123 | MIR30E | −0.2759666 | −0.1673701 | Cancer DR |
| 99 | 138008 | HAND2 | −0.7726292 | −0.6345135 | Cancer DR |
| 100 | 177432 | CASP7 | −10.080261 | −9.8616229 | Cancer DR |
| 101 | 1696 | ZNF347 | 3.20338016 | 3.42245148 | Cancer DR |
| 102 | 40864 | LOC653598 | 29.5211839 | 29.9100599 | Cancer DR |
| 103 | 33044 | LOC401238 | −6.4844928 | −6.2037945 | Cancer DR |
| 104 | 39554 | LOC440014 | −0.4051124 | −0.2520049 | Cancer DR |

TABLE 1-continued

Signature 1

| Signature 1 marker # | Illumina Transcript ID | Gene name | Aggressive cancer mean | Normal mean | Upregulated (UR) or downregulated (DR) in aggressive cancer |
|---|---|---|---|---|---|
| 105 | 175279 | LOC339352 | 14.5986659 | 14.8643875 | Cancer DR |
| 106 | 23490 | NEK7 | −5.929757 | −5.8008051 | Cancer DR |
| 107 | 181743 | LOC646463 | −4.1358791 | −3.8487266 | Cancer DR |
| 108 | 15634 | CCL8 | −73.189981 | −71.419617 | Cancer DR |
| 109 | 34049 | LOC642196 | 3.6810006 | −2.3531877 | Cancer UR |
| 110 | 79403 | HS.157344 | 10.0794538 | 10.4426597 | Cancer DR |
| 111 | 7196 | DHX9 | −4.7593833 | −3.934944 | Cancer DR |
| 112 | 44285 | LOC388237 | 1.03869502 | 1.19389418 | Cancer DR |
| 113 | 178108 | KCNJ14 | 0.41681205 | 0.56043169 | Cancer DR |
| 114 | 166167 | OR7G3 | −0.6721556 | −0.5410997 | Cancer DR |
| 115 | 18273 | GLTSCR1 | 33.8096356 | 34.5040224 | Cancer DR |
| 116 | 1736 | NOMO2 | −112.57512 | −109.84641 | Cancer DR |
| 117 | 175566 | WDR37 | 42.7679257 | 46.0837328 | Cancer DR |

Example 2: Identification of Signature 2

Figure 2:
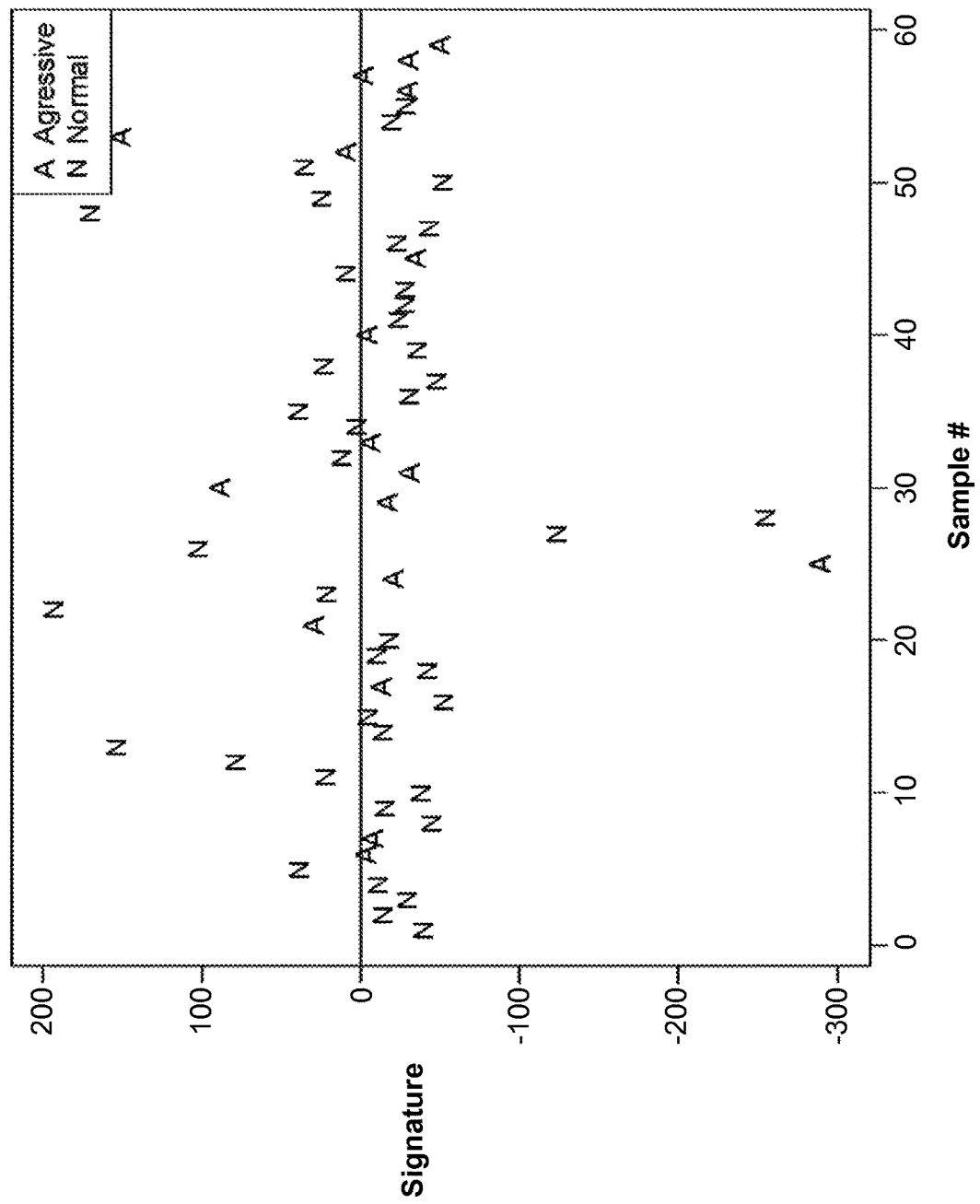
FIG. 2 depicts microarray results in search for a signature of normal (N) vs. aggressive (A) cancer in subtraction-normalized expression data collected from blood samples processed 4 hours after collection. The assay was used to search for stable transcripts (defined as those in the top 1,000 differentially expressed genes, with subtraction normalization at 4 hours) that had an expression level ratio of 0.8 to 1.25 in samples processed 48 hours after collection compared to 4 hours after collection.

A microarray was used to search for a signature of normal vs. aggressive cancer in subtraction-normalized expression data collected from blood samples processed 4 hours after collection. The assay was used to search for stable transcripts (defined as those in the top 1,000 differentially expressed genes, with subtraction normalization at 4 hours) that had an expression level ratio of 0.8 to 1.25 in samples processed 48 hours after collection compared to 4 hours after collection (FIG. 2). Based on this assay, 18 genes were selected and cross validated as described in Example 5, below. Signature 2 had a sensitivity (probability of correctly detecting aggressive cancer) of 60%, and a specificity (probability of correctly identifying normal patients) of 66%.

TABLE 2

Signature 2

| Signature 2 marker # | Illumina Transcript ID | Gene name | Aggressive cancer mean | Normal mean | Upregulated (UR) or downregulated (DR) in aggressive cancer |
|---|---|---|---|---|---|
| 1 | 175412 | REPS2 | 0.14613724 | −7.5068116 | Cancer UR |
| 2 | 33909 | LOC285588 | 3.2824067 | −1.8452802 | Cancer UR |
| 3 | 22438 | C20ORF112 | 2.62604692 | −4.0643154 | Cancer UR |
| 4 | 337363 | DIPAS | 1.06084697 | −3.2177178 | Cancer UR |
| 5 | 165657 | TPRX1 | 1.79654397 | −2.8351934 | Cancer UR |
| 6 | 38966 | FLJ16369 | 1.13600879 | −2.5978003 | Cancer UR |
| 7 | 44021 | LOC652255 | 3.03708564 | −1.7358787 | Cancer UR |
| 8 | 41116 | LOC642130 | 2.03361554 | −1.9989049 | Cancer UR |
| 9 | 21343 | DPRX | 2.98927307 | −2.5628675 | Cancer UR |
| 10 | 339666 | LOC440225 | 1.72985119 | −2.6607478 | Cancer UR |
| 11 | 91353 | HS.434989 | 1.08668984 | −2.5889165 | Cancer UR |
| 12 | 40621 | LOC642335 | 2.69733599 | −2.2656365 | Cancer UR |
| 13 | 369972 | GGTLC1 | 1.04843521 | −3.889128 | Cancer UR |
| 14 | 32275 | LOC642966 | 4.72677994 | −2.0890642 | Cancer UR |
| 15 | 22944 | NKX6-1 | 2.1845754 | −2.4379099 | Cancer UR |
| 16 | 17458 | GPC5 | 0.40241623 | −4.2203747 | Cancer UR |
| 17 | 13240 | RASGEF1C | 0.83201981 | −3.3957263 | Cancer UR |
| 18 | 22752 | ACOT11 | 2.83207957 | −2.2946388 | Cancer UR |

Example 3: Identification of Signature 3

A microarray was used as in Example 2 to search for a signature of normal vs. aggressive cancer in subtraction-normalized expression data collected from blood samples processed 4 hours after collection. Based on this assay, 18 genes were selected and cross validated as described in Example 5, below. Signature 3 had a sensitivity (probability of correctly detecting aggressive cancer) of 45%, and a specificity (probability of correctly identifying normal patients) of 64%.

TABLE 3

Signature 3

| Signature 3 marker # | Illumina Transcript ID | Gene name | Aggressive cancer mean | Normal mean | Upregulated (UR) or downregulated (DR) in aggressive cancer |
|---|---|---|---|---|---|
| 1 | 175412 | REPS2 | 0.14613724 | −7.5068116 | Cancer UR |
| 2 | 33909 | LOC285588 | 3.2824067 | −1.8452802 | Cancer UR |
| 3 | 22438 | C20ORF112 | 2.62604692 | −4.0643154 | Cancer UR |
| 4 | 337363 | DIPAS | 1.06084697 | −3.2177178 | Cancer UR |
| 5 | 165657 | TPRX1 | 1.79654397 | −2.8351934 | Cancer UR |
| 6 | 38966 | FLJ16369 | 1.13600879 | −2.5978003 | Cancer UR |
| 7 | 44021 | LOC652255 | 3.03708564 | −1.7358787 | Cancer UR |
| 8 | 41116 | LOC642130 | 2.03361554 | −1.9989049 | Cancer UR |
| 9 | 21343 | DPRX | 2.98927307 | −2.5628675 | Cancer UR |
| 10 | 339666 | LOC440225 | 1.72985119 | −2.6607478 | Cancer UR |
| 11 | 91353 | HS.434989 | 1.08668984 | −2.5889165 | Cancer UR |
| 12 | 40621 | LOC642335 | 2.69733599 | −2.2656365 | Cancer UR |
| 13 | 369972 | GGTLC1 | 1.04843521 | −3.889128 | Cancer UR |
| 14 | 32275 | LOC642966 | 4.72677994 | −2.0890642 | Cancer UR |
| 15 | 22944 | NKX6-1 | 2.1845754 | −2.4379099 | Cancer UR |
| 16 | 17458 | GPC5 | 0.40241623 | −4.2203747 | Cancer UR |
| 17 | 13240 | RASGEF1C | 0.83201981 | −3.3957263 | Cancer UR |
| 18 | 22752 | ACOT11 | 2.83207957 | −2.2946388 | Cancer UR |

Example 4: Identification of Signature 4

A microarray was used to search for a signature of normal vs. aggressive cancer in subtraction-normalized expression data collected from blood samples processed 4 hours after collection. Based on this assay, the 10 genes of Signature 4 were selected and cross validated as described in Example 5, below. Signature 4 had a sensitivity (probability of correctly detecting aggressive cancer) of 64%, and a specificity (probability of correctly identifying normal patients) of 58%.

TABLE 4

Signature 4

| Signature 4 marker # | Illumina Transcript ID | Gene name | Aggressive cancer mean | Normal mean | Upregulated (UR) or downregulated (DR) in aggressive cancer |
|---|---|---|---|---|---|
| 1 | 8276 | C3ORF26 | 7.1783549 | −54.138047 | Cancer UR |
| 2 | 22171 | FOXA3 | 3.2824067 | −1.8452802 | Cancer UR |
| 3 | 1150 | FANCB | 4.67348819 | −1.6783285 | Cancer UR |
| 4 | 162004 | ALDH9A1 | 4.70953157 | −1.8584848 | Cancer UR |
| 5 | 334559 | LOC100133080 | 4.69638401 | −1.994684 | Cancer UR |
| 6 | 19987 | NR2E1 | 3.75650279 | −2.8100791 | Cancer UR |
| 7 | 90347 | HS.413397 | 2.45548587 | −2.5067911 | Cancer UR |
| 8 | 7726 | NSUN7 | 2.1845754 | −2.4379099 | Cancer UR |
| 9 | 34808 | LOC651044 | 2.37077671 | −2.1346992 | Cancer UR |
| 10 | 364878 | PCBP2 | 3.6810006 | −2.3531877 | Cancer UR |

Example 5: Statistical Analysis of Microarray Data

Working with microarray data can be challenging because large numbers of genes can increase the likelihood of false positives, while a small number of samples can lead to overfitting. These issues can be overcome by using statistical methods to reduce the false rate of positives and using independent training and test data sets (e.g., cross-validation) to avoid overfitting. In particular, instead of using a "typical" 5% significance level, the false discovery rate (FDR) can be controlled to ensure that only 5% of the genes that are discovered are false positives, and Empirical Bayesian estimates can be used to improve test statistics.

Because an overfit model will perform poorly on an independent test set, a good test of the fit of a model is how well is performs on an independent test set. For small sample sizes, splitting data into test and training sets may leave too small of a data set for good training. This issue can be solved by using cross-validation, which splits the data into K-folds, trains the method on K−1 of the folds, and tests the method on the last fold. The ideal split for cross-validation is 10-fold for accurate and precise estimates of diagnostic accuracy. In a 10-fold cross validation, however, there are more than 10 splits because there are many choices for which data points go into the folds. For example, with the microarray data collected as described above, there are 50,979,600 ways to form 90% training/10% testing data sets.

The Empirical Bayesian method was used as follows:

1. The differential gene expression (DE) of macrophages vs. T cells was calculated for each gene. DE is expressed as the log of the ratio of phagocyte to T cell expression: $DE=\log(GE_P/GE_{TC})$, where $GE_P$ is phagocyte gene expression and $GE_{TC}$ is T cell gene expression.

2. The mean DE was compared in cancer and control patients with a two-sample t-test. Empirical Bayes estimates of the test statistics "shrink" these toward zero.
3. Calculate a diagnostic signature with K genes:

$$S = \sum_{i=1}^{K} w_i(DE_i - \mu_i)$$

If S>0, then the patient was diagnosed with cancer.

4. The number of genes K to include in the signature was determined by comparing misclassification rates in independent test sets with cross-validation.

Errors were calculated using an average of 1-sensitivity and 1-specificity, and the cross-validated error was used to select markers.

Using the above methods, the markers associated with aggressive prostate cancer in macrophages vs. T cells (Tables 1 and 2) were identified.

What is claimed is:

1. A method for identifying the efficacy of a treatment for prostate cancer in a subject diagnosed with prostate cancer, wherein said treatment is administered to said subject, comprising:
   a) measuring the levels of gene expression of ten or more markers comprising OAS3, RPL13L, RDH5, SOX6, OSBPL1A, GPS, GPR89A, TMEM80, PPPDE2, RYR3 in a population of the subject's macrophage cells and/or neutrophil cells at a first time point;
   b) measuring the levels of gene expression of the ten or more markers in a population of the subject's non-phagocytic cells at the same first time point;
   c) identifying a first difference between the measured levels of gene expression of the ten or more markers in steps a) and b);
   d) measuring the levels of gene expression of the ten or more markers in a population of the subject's macrophage cells and/or neutrophil cells at a second time point;
   e) measuring the levels of gene expression of the ten or more markers in a population of the subject's non-phagocytic cells at the same second time point;
   f) identifying a second difference between the measured levels of gene expression of the ten or more markers in steps d) and e); and
   g) identifying the presence of a third difference, wherein said third difference is a difference between the first difference and the second difference.

2. The method of claim 1, wherein the first time point is before the treatment commences.

3. The method of claim 1, wherein the second time point is after the treatment commences.

4. The method of claim 1, wherein the second time point is after the treatment ends.

5. The method of claim 1, further comprising measuring at least one standard parameter associated with said prostate cancer.

6. The method of claim 5, wherein the standard parameter is selected from the group consisting of tumor stage, tumor grade, tumor size, tumor visual characteristics, tumor growth, tumor thickness, tumor progression, tumor metastasis tumor distribution within the body, odor, molecular pathology, genomics, or tumor angiograms.

7. A method for identifying the progression or regression of a prostate cancer in a subject, comprising:
   a) measuring the levels of gene expression of ten or more markers comprising OAS3, RPL13L, RDH5, SOX6, OSBPL1A, GPS, GPR89A, TMEM80, PPPDE2, RYR3 in a population of the subject's macrophage cells and/or neutrophil cells at a first time point;
   b) measuring the levels of gene expression of the ten or more markers in a population of the subject's non-phagocytic cells at the same first time point;
   c) identifying a first difference between the measured levels of gene expression of the ten or more markers in steps a) and b);
   d) measuring the levels of gene expression of the ten or more markers in a population of the subject's macrophage cells and/or neutrophil cells at a second time point;
   e) measuring the levels of gene expression of the ten or more markers in a population of the subject's non-phagocytic cells at the same second time point;
   f) identifying a second difference between the measured levels of gene expression of the ten or more markers in steps d) and e); and
   g) identifying the presence of a third difference, wherein said third difference is a difference between the first difference and the second difference.

8. The method of claim 7, further comprising measuring at least one standard parameter associated with said prostate cancer.

9. The method of claim 8, wherein the standard parameter is selected from the group consisting of tumor stage, tumor grade, tumor size, tumor visual characteristics, tumor growth, tumor thickness, tumor progression, tumor metastasis tumor distribution within the body, odor, molecular pathology, genomics, or tumor angiograms.

* * * * *

UNITED STATES PATENT AND TRADEMARK OFFICE
CERTIFICATE OF CORRECTION

PATENT NO. : 10,626,464 B2
APPLICATION NO. : 15/510948
DATED : April 21, 2020
INVENTOR(S) : Kassis et al.

Page 1 of 1

It is certified that error appears in the above-identified patent and that said Letters Patent is hereby corrected as shown below:

In the Claims

Claim 1, Column 49, Line 30 reads:
"OSBPL1A, GPS, GPR89A, TMEM80, PPPDE2,"

Whereas it should read:
"OSBPL1A, GP5, GPR89A, TMEM80, PPPDE2,"

And

Claim 7, Column 50, Line 19 reads:
"OSBPL1A, GPS, GPR89A, TMEM80, PPPDE2,"

Whereas it should read:
"OSBPL1A, GP5, GPR89A, TMEM80, PPPDE2,"

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*